United States Patent
Laurent et al.

(10) Patent No.: US 11,439,398 B2
(45) Date of Patent: *Sep. 13, 2022

(54) RELEASE MECHANISM FOR LINEAR SURGICAL STAPLER

(71) Applicant: Cilag GmbH International, Zug (CH)

(72) Inventors: Ryan J. Laurent, Loveland, OH (US); Michael J. Stokes, Cicninnati, OH (US); Matthew S. Corbin, Brea, CA (US)

(73) Assignee: Cilag GmbH International, Zug (CH)

( * ) Notice: Subject to any disclaimer, the term of this patent is extended or adjusted under 35 U.S.C. 154(b) by 159 days.

This patent is subject to a terminal disclaimer.

(21) Appl. No.: 16/836,262

(22) Filed: Mar. 31, 2020

(65) Prior Publication Data

US 2020/0289120 A1  Sep. 17, 2020

Related U.S. Application Data

(63) Continuation of application No. 15/889,363, filed on Feb. 6, 2018, now Pat. No. 10,631,866.

(51) Int. Cl.
*A61B 17/072* (2006.01)
*A61B 17/115* (2006.01)
(Continued)

(52) U.S. Cl.
CPC .......... *A61B 17/115* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 17/115; A61B 17/0644;
(Continued)

(56) References Cited

U.S. PATENT DOCUMENTS

| 960,300 A | 6/1910 | Fischer |
|---|---|---|
| 3,078,465 A | 2/1963 | Bobrov |

(Continued)

FOREIGN PATENT DOCUMENTS

| CN | 103263282 B | 8/2013 |
|---|---|---|
| EP | 0033548 B1 | 5/1986 |

(Continued)

OTHER PUBLICATIONS

European Search Report, Extended, and Written Opinion dated Jun. 28, 2019 for Application No. 19155568.9, 9 pages.

(Continued)

*Primary Examiner* — Scott A Smith
(74) *Attorney, Agent, or Firm* — Frost Brown Todd LLC

(57) ABSTRACT

An apparatus includes a handle assembly, an end effector, a firing assembly, and a release assembly. The handle assembly includes first and second arms and a latching lever. The end effector includes first and second jaws. The firing assembly is configured to sever tissue captured between the jaws. The release assemble is configured to urge the latching lever away from the first arm to pivot the second jaw from a fully closed position to a partially closed position.

20 Claims, 26 Drawing Sheets

(51) Int. Cl.
*A61B 17/11* (2006.01)
*A61B 17/3205* (2006.01)
A61B 17/068 (2006.01)
A61B 17/00 (2006.01)

(52) U.S. Cl.
CPC ...... *A61B 17/1114* (2013.01); *A61B 17/3205* (2013.01); *A61B 17/068* (2013.01); A61B 2017/00477 (2013.01); A61B 2017/0725 (2013.01); A61B 2017/07214 (2013.01); A61B 2017/07271 (2013.01); A61B 2017/07285 (2013.01)

(58) Field of Classification Search
CPC ........... A61B 2017/00477; A61B 2017/07214; A61B 2017/07271; A61B 2017/07285
USPC .. 227/19, 175.1, 176.1, 175.2, 175.3, 180.1; 606/1, 139, 153, 213, 219
See application file for complete search history.

(56) References Cited

U.S. PATENT DOCUMENTS

| | | |
|---|---|---|
| 3,079,606 A | 3/1963 | Bobrov et al. |
| 3,315,863 A | 4/1967 | O'Dea |
| 3,317,105 A | 5/1967 | Astafjev et al. |
| 3,490,675 A | 1/1970 | Green et al. |
| 4,111,206 A | 9/1978 | Vishnevsky et al. |
| 4,241,861 A | 12/1980 | Fleischer |
| 4,290,542 A | 9/1981 | Fedotov et al. |
| D272,851 S | 2/1984 | Green et al. |
| D272,852 S | 2/1984 | Green et al. |
| 4,429,695 A | 2/1984 | Green |
| 4,520,817 A | 6/1985 | Green |
| 4,596,351 A | 6/1986 | Fedotov et al. |
| 4,605,001 A | 8/1986 | Rothfuss et al. |
| D285,836 S | 9/1986 | Hunt et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,869,415 A | 9/1989 | Fox |
| 4,892,244 A | 1/1990 | Fox et al. |
| 4,955,898 A | 9/1990 | Matsutani et al. |
| 5,065,929 A | 11/1991 | Schulze et al. |
| 5,083,695 A | 1/1992 | Foslien et al. |
| 5,129,570 A | 7/1992 | Schulze et al. |
| 5,141,144 A | 8/1992 | Foslien et al. |
| 5,156,614 A | 10/1992 | Green et al. |
| 5,173,133 A | 12/1992 | Morin et al. |
| 5,180,092 A | 1/1993 | Crainich |
| 5,188,274 A | 2/1993 | Moeinzadeh et al. |
| 5,221,036 A | 6/1993 | Takase |
| 5,395,034 A | 3/1995 | Allen et al. |
| 5,417,361 A | 5/1995 | Williamson, IV |
| 5,445,304 A | 8/1995 | Plyley et al. |
| 5,452,837 A | 9/1995 | Williamson, IV et al. |
| 5,465,896 A | 11/1995 | Allen et al. |
| 5,489,058 A | 2/1996 | Plyley et al. |
| 5,505,363 A | 4/1996 | Green et al. |
| 5,535,935 A | 7/1996 | Vidal et al. |
| 5,542,594 A | 8/1996 | McKean et al. |
| 5,562,241 A | 10/1996 | Knodel et al. |
| 5,586,711 A | 12/1996 | Plyley et al. |
| 5,636,779 A | 6/1997 | Palmer |
| 5,651,491 A | 7/1997 | Heaton et al. |
| 5,653,373 A | 8/1997 | Green et al. |
| 5,655,698 A | 8/1997 | Yoon |
| 5,657,921 A | 8/1997 | Young et al. |
| 5,673,842 A | 10/1997 | Bittner et al. |
| 5,680,983 A | 10/1997 | Plyley et al. |
| 5,718,359 A | 2/1998 | Palmer et al. |
| 5,785,232 A | 7/1998 | Vidal et al. |
| 5,816,471 A | 10/1998 | Plyley et al. |
| 5,871,135 A | 2/1999 | Williamson, IV et al. |
| 5,878,938 A * | 3/1999 | Bittner ............ A61B 17/07207 227/175.4 |
| 5,908,427 A | 6/1999 | McKean et al. |
| 5,988,479 A | 11/1999 | Palmer |
| 6,045,560 A | 4/2000 | McKean et al. |
| 6,131,789 A | 10/2000 | Schulze et al. |
| 6,155,473 A | 12/2000 | Tompkins et al. |
| 6,206,903 B1 | 3/2001 | Ramans |
| 7,032,799 B2 | 4/2006 | Viola et al. |
| 7,055,730 B2 | 6/2006 | Ehrenfels et al. |
| 7,121,446 B2 | 10/2006 | Arad et al. |
| 7,140,527 B2 | 11/2006 | Ehrenfels et al. |
| 7,188,758 B2 | 3/2007 | Viola et al. |
| 7,207,471 B2 | 4/2007 | Heinrich et al. |
| 7,210,609 B2 | 5/2007 | Leiboff et al. |
| 7,238,195 B2 | 7/2007 | Viola |
| 7,278,563 B1 | 10/2007 | Green |
| 7,293,685 B2 | 11/2007 | Ehrenfels et al. |
| 7,326,232 B2 | 2/2008 | Viola et al. |
| 7,334,717 B2 | 2/2008 | Rethy et al. |
| 7,407,078 B2 | 8/2008 | Shelton, IV et al. |
| 7,419,081 B2 | 9/2008 | Ehrenfels et al. |
| 7,422,139 B2 | 9/2008 | Shelton, IV et al. |
| 7,431,730 B2 | 10/2008 | Viola |
| 7,472,815 B2 | 1/2009 | Shelton, IV et al. |
| 7,472,816 B2 | 1/2009 | Holsten et al. |
| 7,490,749 B2 | 2/2009 | Schall et al. |
| 7,543,729 B2 | 6/2009 | Ivanko |
| 7,568,604 B2 | 8/2009 | Ehrenfels et al. |
| 7,571,845 B2 | 8/2009 | Viola |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,410 B2 | 12/2009 | Marczyk |
| 7,641,091 B2 | 1/2010 | Olson et al. |
| 7,665,647 B2 | 2/2010 | Shelton, IV et al. |
| 7,717,312 B2 | 5/2010 | Beetel |
| 7,721,933 B2 | 5/2010 | Ehrenfels et al. |
| 7,722,610 B2 | 5/2010 | Viola et al. |
| 7,740,160 B2 | 6/2010 | Viola |
| 7,744,628 B2 | 6/2010 | Viola |
| 7,766,209 B2 | 8/2010 | Baxter, III et al. |
| 7,810,691 B2 | 10/2010 | Boyden et al. |
| 7,815,092 B2 | 10/2010 | Whitman et al. |
| 7,828,189 B2 | 11/2010 | Holsten et al. |
| 7,832,612 B2 * | 11/2010 | Baxter, III .......... A61B 17/105 227/175.2 |
| 7,837,081 B2 | 11/2010 | Holsten et al. |
| 7,866,528 B2 | 1/2011 | Olson et al. |
| 7,905,381 B2 | 3/2011 | Baxter, III et al. |
| 7,931,182 B2 | 4/2011 | Boyden et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,997,469 B2 | 8/2011 | Olson et al. |
| 8,006,888 B2 | 8/2011 | Viola |
| 8,028,884 B2 | 10/2011 | Sniffin et al. |
| 8,070,035 B2 | 12/2011 | Holsten et al. |
| 8,074,861 B2 | 12/2011 | Ehrenfels et al. |
| 8,091,754 B2 | 1/2012 | Ehrenfels et al. |
| 8,113,407 B2 | 2/2012 | Holsten et al. |
| 8,127,975 B2 | 3/2012 | Olson et al. |
| 8,141,762 B2 | 3/2012 | Bedi et al. |
| 8,152,041 B2 | 4/2012 | Kostrzewski |
| 8,157,153 B2 | 4/2012 | Shelton, IV et al. |
| 8,205,781 B2 | 6/2012 | Baxter, III et al. |
| 8,231,040 B2 | 7/2012 | Zemlok et al. |
| 8,245,901 B2 | 8/2012 | Stopek |
| 8,256,655 B2 | 9/2012 | Sniffin et al. |
| 8,257,634 B2 | 9/2012 | Scirica |
| 8,267,300 B2 | 9/2012 | Boudreaux |
| 8,272,552 B2 | 9/2012 | Holsten et al. |
| 8,292,146 B2 | 10/2012 | Holsten et al. |
| 8,292,148 B2 | 10/2012 | Viola |
| 8,308,043 B2 | 11/2012 | Bindra et al. |
| 8,336,753 B2 | 12/2012 | Olson et al. |
| 8,348,129 B2 | 1/2013 | Bedi et al. |
| 8,418,907 B2 | 4/2013 | Johnson et al. |
| 8,453,908 B2 | 6/2013 | Bedi et al. |

(56) References Cited

U.S. PATENT DOCUMENTS

| | | |
|---|---|---|
| 8,464,922 B2 | 6/2013 | Marczyk |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,505,801 B2 | 8/2013 | Ehrenfels et al. |
| 8,544,712 B2 | 10/2013 | Jankowski |
| 8,579,178 B2 | 11/2013 | Holsten et al. |
| 8,636,193 B2 | 1/2014 | Whitman et al. |
| 8,636,939 B2 | 1/2014 | Czernik et al. |
| 8,679,156 B2 | 3/2014 | Smith et al. |
| 8,708,210 B2 | 4/2014 | Zemlok et al. |
| 8,728,118 B2 | 5/2014 | Hinman et al. |
| 8,789,740 B2 | 7/2014 | Baxter, III et al. |
| 8,905,287 B2 | 12/2014 | Racenet et al. |
| 8,915,930 B2 | 12/2014 | Huitema et al. |
| 9,016,541 B2 | 4/2015 | Viola et al. |
| 9,119,617 B2 | 9/2015 | Souls et al. |
| 9,155,537 B2 | 10/2015 | Katre et al. |
| 9,271,728 B2 | 3/2016 | Gupta et al. |
| 9,289,209 B2 | 3/2016 | Gurumurthy et al. |
| 9,364,219 B2 | 6/2016 | Olson et al. |
| 9,402,629 B2 | 8/2016 | Ehrenfels et al. |
| 9,439,649 B2 | 9/2016 | Shelton, IV et al. |
| 9,451,959 B2 | 9/2016 | Patankar et al. |
| 9,474,525 B2 | 10/2016 | Smith et al. |
| 9,498,213 B2 | 11/2016 | Marczyk et al. |
| 9,561,030 B2 | 2/2017 | Zhang et al. |
| 9,629,812 B2 | 4/2017 | Widenhouse et al. |
| 9,636,113 B2 | 5/2017 | Wenchell |
| 9,636,128 B2 | 5/2017 | Zemlok et al. |
| 9,681,873 B2 | 6/2017 | Smith et al. |
| 9,693,775 B2 | 7/2017 | Agarwal et al. |
| 9,750,502 B2 | 9/2017 | Scirica et al. |
| 9,867,616 B2 | 1/2018 | Marczyk |
| 10,631,866 B2 | 4/2020 | Laurent et al. |
| 10,667,818 B2 | 6/2020 | McLain et al. |
| 10,687,819 B2 | 6/2020 | Stokes et al. |
| 10,874,398 B2 | 12/2020 | Baxter, III et al. |
| 10,898,197 B2 | 1/2021 | Baxter, III et al. |
| 10,932,781 B2 | 3/2021 | Jones et al. |
| 11,219,454 B2 * | 1/2022 | Schings ............... A61B 17/1114 |
| 2005/0222616 A1 | 10/2005 | Rethy et al. |
| 2006/0180633 A1 | 8/2006 | Emmons |
| 2007/0119901 A1 | 5/2007 | Ehrenfels et al. |
| 2007/0145096 A1 | 6/2007 | Viola et al. |
| 2009/0255974 A1 | 10/2009 | Viola |
| 2009/0308907 A1 | 12/2009 | Nalagatla et al. |
| 2010/0133317 A1 | 6/2010 | Shelton, IV et al. |
| 2011/0290856 A1 | 12/2011 | Shelton, IV et al. |
| 2012/0046689 A1 | 2/2012 | Crisuolo et al. |
| 2012/0286022 A1 | 11/2012 | Olson et al. |
| 2013/0037595 A1 | 2/2013 | Gupta et al. |
| 2013/0186935 A1 | 7/2013 | Edoga et al. |
| 2013/0190732 A1 | 7/2013 | Slisz et al. |
| 2014/0103091 A1 | 4/2014 | Whitman et al. |
| 2014/0353357 A1 | 12/2014 | Agarwal et al. |
| 2015/0327855 A1 | 11/2015 | Katre et al. |
| 2016/0157890 A1 | 6/2016 | Drake et al. |
| 2016/0262756 A1 | 9/2016 | Patankar et al. |
| 2019/0239883 A1* | 8/2019 | Baxter, III ............ A61B 17/115 |
| 2019/0239885 A1* | 8/2019 | Stokes ............. A61B 17/07207 |
| 2020/0046351 A1* | 2/2020 | Jones ................... A61B 17/072 |
| 2020/0046353 A1* | 2/2020 | Deck ................ A61B 17/07207 |
| 2020/0113562 A1* | 4/2020 | Schings ............... A61B 17/072 |

FOREIGN PATENT DOCUMENTS

| | | |
|---|---|---|
| EP | 0178940 B1 | 1/1991 |
| EP | 0669104 A1 | 8/1995 |
| EP | 0770355 A1 | 5/1997 |
| EP | 1382303 B1 | 6/2006 |
| EP | 1702567 A2 | 9/2006 |
| EP | 1728475 A2 | 12/2006 |
| EP | 1977701 B1 | 12/2011 |
| EP | 2452636 A2 | 5/2012 |
| EP | 2305137 B1 | 12/2012 |
| EP | 2308390 B1 | 12/2012 |
| EP | 1693007 B1 | 10/2013 |
| EP | 1862129 B1 | 4/2014 |
| EP | 2550920 B1 | 1/2015 |
| EP | 2532313 B1 | 4/2016 |
| EP | 2532312 B1 | 12/2016 |
| EP | 3155988 A1 | 4/2017 |
| GB | 927936 A | 6/1963 |
| JP | 2001-502575 A | 2/2001 |
| JP | 2007-000657 A | 1/2007 |
| SU | 599799 A1 | 4/1978 |
| WO | WO 1999/045849 A1 | 9/1999 |
| WO | WO 2002/030297 A2 | 4/2002 |
| WO | WO 2003/030742 A2 | 4/2003 |
| WO | WO 2003/094743 A1 | 11/2003 |
| WO | WO 2003/094745 A1 | 11/2003 |
| WO | WO 2003/094746 A1 | 11/2003 |
| WO | WO 2003/094747 A1 | 11/2003 |
| WO | WO 2003/079909 A3 | 3/2004 |
| WO | WO 2004/032763 A2 | 4/2004 |
| WO | WO 2007/127283 A2 | 11/2007 |
| WO | WO 2013/022703 A1 | 2/2013 |
| WO | WO 2015/065485 A1 | 5/2015 |

OTHER PUBLICATIONS

International Search Report and Written Opinion dated Jun. 3, 2019 for International Application No. PCT/IB2019/050356, 12 pages.

* cited by examiner

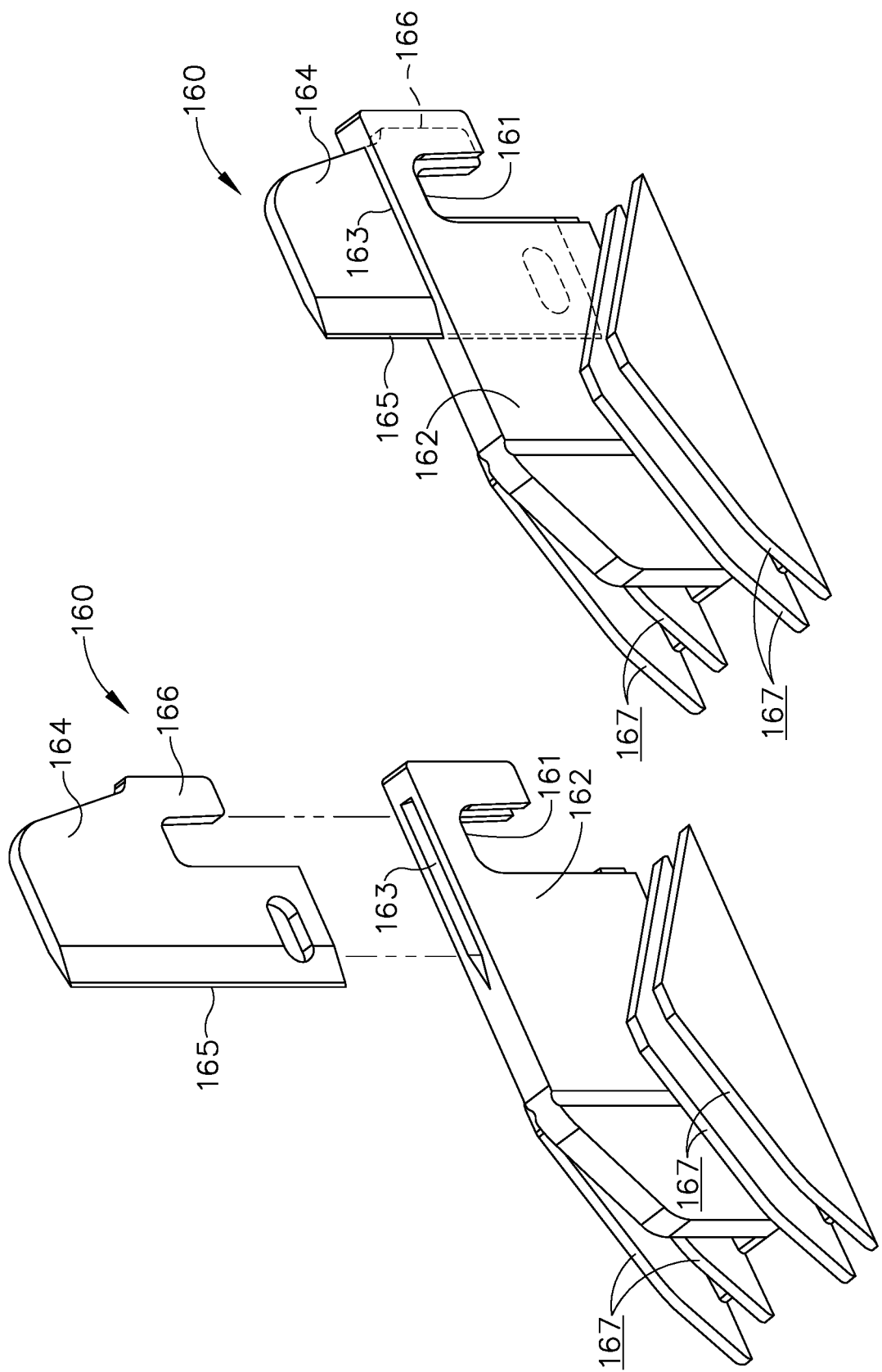

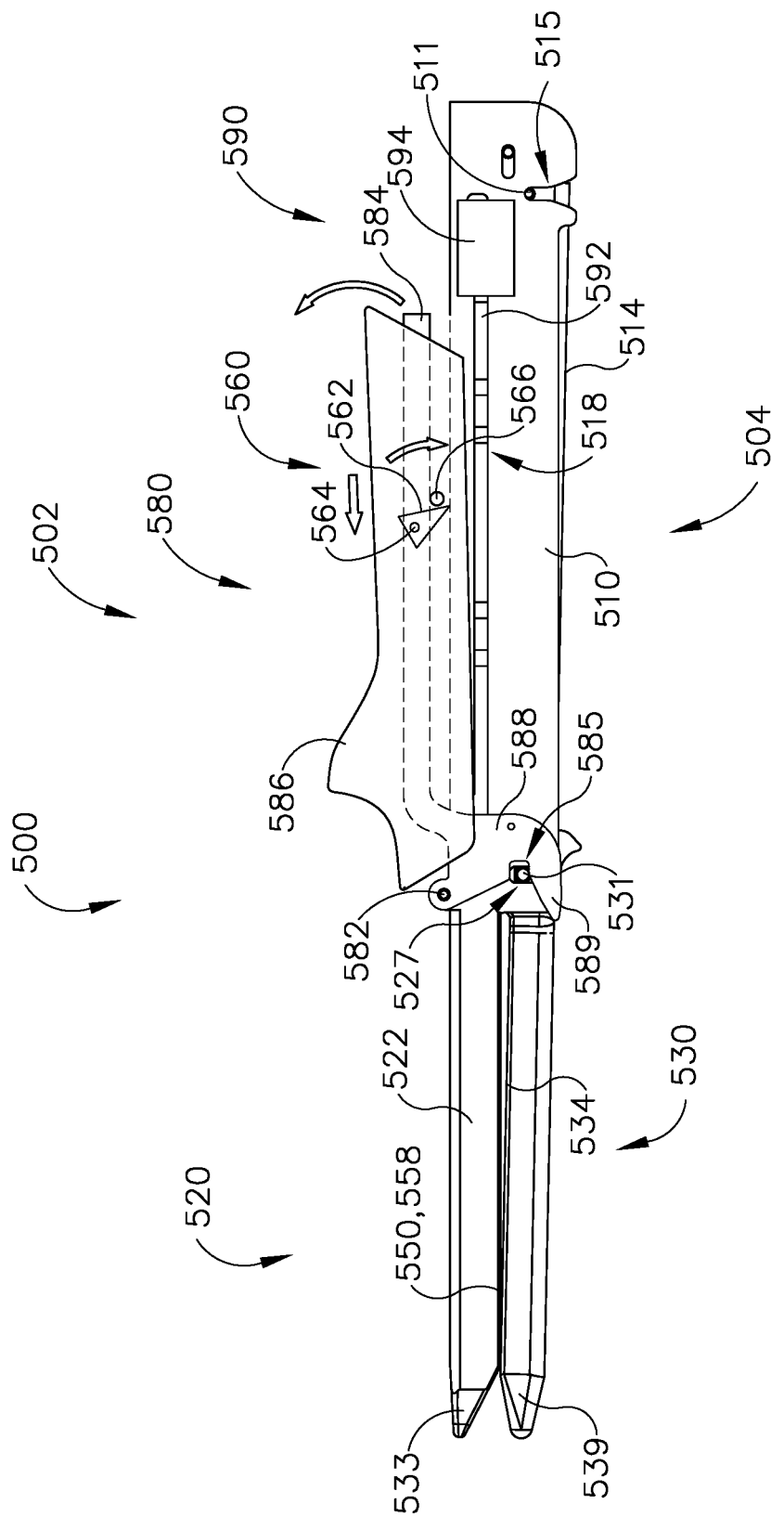

RELEASE MECHANISM FOR LINEAR SURGICAL STAPLER

This application is a continuation of U.S. patent application Ser. No. 15/889,363, filed Feb. 6, 2018 and issued as U.S. Pat. No. 10,631,866 on Apr. 28, 2020.

BACKGROUND

In some surgical operations, such as a gastrointestinal anastomosis, it may be desirable to clamp down on one or more layers of tissue, cut through the clamped layers of tissue and drive staples through the layers of tissue to substantially seal the severed layers of tissue together near the severed ends of the tissue layers. One such instrument that may be used in such operations is a linear cutting stapler. A linear cutting stapler generally includes a first jaw, a second jaw, a lever for clamping the first jaw relative to the second jaw, an anvil associated with either the first jaw or the second jaw, a staple cartridge associated with the jaw opposing the staple anvil, and a firing assembly movable relative to the rest of the linear cutting stapler. The first jaw and the second jaw may pivot relative each other in order to grasp tissue between the jaws. Staples are arranged in the staple cartridge such that a portion of firing assembly may actuate through the staple cartridge to drive staples out of staple cartridge, through the tissue, and against anvil while also severing tissue captured between the staple cartridge and the staple anvil.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts an exploded view of a staple sled assembly of the surgical stapling instrument of FIG. 1;

FIG. 8 depicts a perspective view of the staple sled assembly of FIG. 7;

FIG. 15C depicts a side elevation view of the surgical instrument of FIG. 14, where the firing assembly is in the unfired position, where the release assembly is in a second position, and where the first portion is coupled with the second portion in a partially released position.

Figure 1:
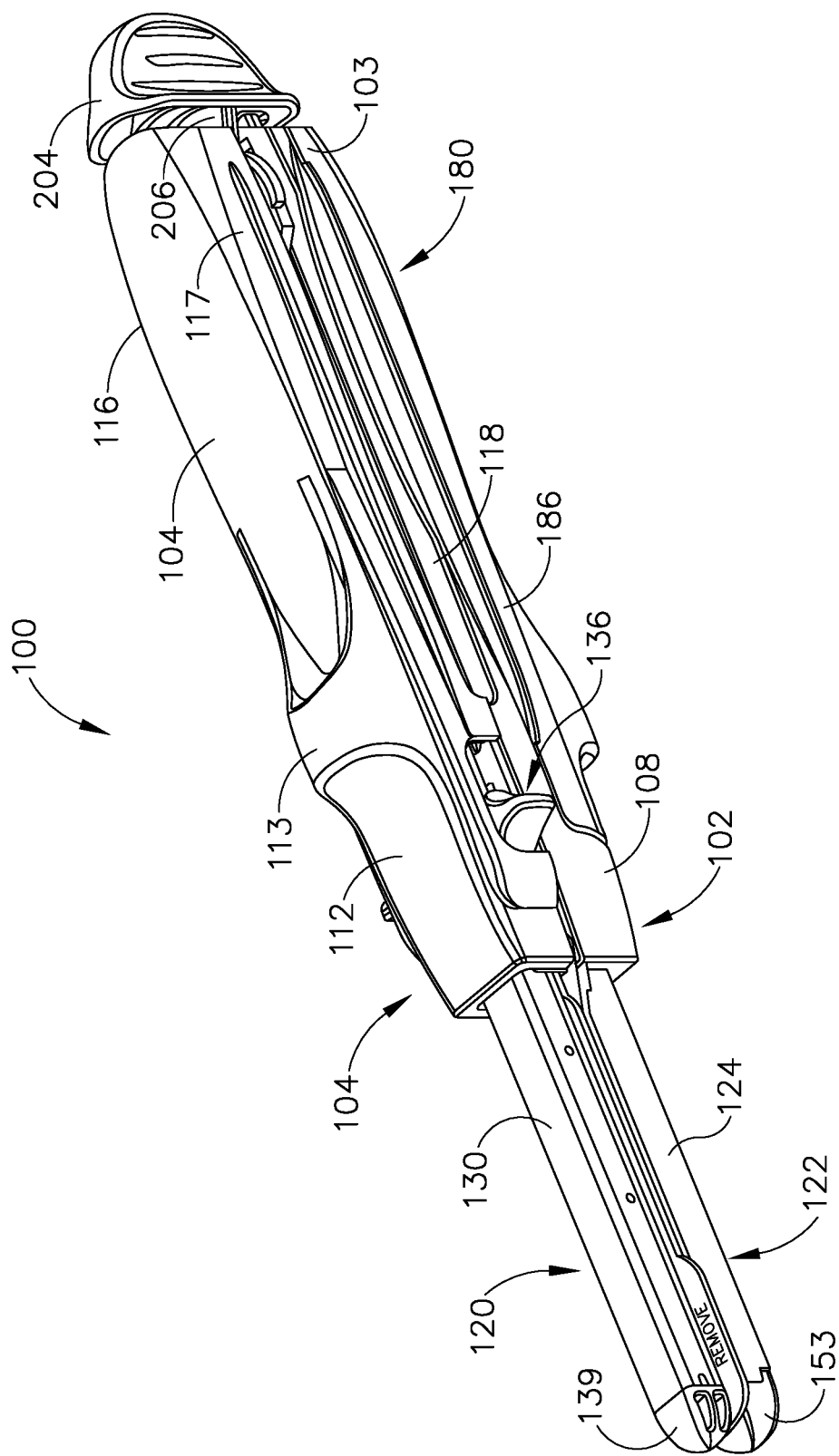
FIG. 1 depicts a perspective view of an exemplary surgical stapling instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal," "distal," "upper," and "lower" are thus relative terms and not intended to unnecessarily limit the invention described herein.

I. Overview of Exemplary Linear Cutting Stapler

FIG. 1 depicts an exemplary surgical linear cutting stapler (100) that may be used for any suitable procedure, such as a gastrointestinal anastomosis. Linear cutting stapler (100) includes a first portion (102) having a staple cartridge channel (122), a second portion (104) having an anvil channel (130), a staple cartridge assembly (150) that may selectively couple with cartridge channel (122) of first portion (102), and a firing assembly (200). As will be described in greater detail below, first portion (102) and staple cartridge assembly (150) may pivotably couple with second portion (104) to form an end effector (120) capable of clamping, severing, and stapling tissue captured between opposing halves of end effector (120).

As best seen in FIGS. 3-6, firing assembly (200) includes an actuating beam (202), a staple sled assembly (160) housed within staple cartridge assembly (150), an actuator (204) (also referred to as a "firing knob"), and a pivot arm (206). Actuating beam (202) extends from a distal end (201) to a proximal end (203). Actuating beam (202) is slidably housed within first portion (102). Pivot arm (206) connects actuator (204) with distal end (201) of actuating beam (202). Actuator (204) and pivot arm (206) may pivot from a proximal position (shown in FIG. 1) to either lateral side of actuating beam (202) (shown in FIG. 11A), thereby enabling an operator to actuate firing assembly (200) from either a first side (116) or a second side (117) of instrument (100) when portions (102, 104) are properly coupled and end effector (120) is in the fully closed position. It should be understood when instrument (100) is properly coupled and end effector (120) is in the fully closed position, first portion (102) and second portion (104) define a slot (118) dimensioned to accommodate translation of actuator (204). In the current example, as will be described in greater detail below, actuating beam (202) is operable to couple with staple sled assembly (160) when staple cartridge assembly (150) is suitably coupled with first portion (102) such that actuator (204) may slide along first side (116) or second side (117) of instrument (100), thereby driving actuating beam (202) and staple sled assembly (160) distally through cartridge assembly (150) to fire instrument (100).

While in the present example, actuator (204) is configured to pivot to either side (116, 117) of instrument (100) to drive actuating beam (202), this is merely optional, as actuator (204) may slidably couple with first portion (102) or second portion (104) through any means apparent to one having ordinary skill in the art in view of the teachings herein. In one example, actuator (204) may strictly associate with first side (116) or second side (117) such that actuator (204) may not pivot when end effector (120) is in the fully closed position. In another example, there may be an actuator (204) positioned on both first side (116) and second side (117), such that instrument (100) may include two actuators (204).

Figure 3:
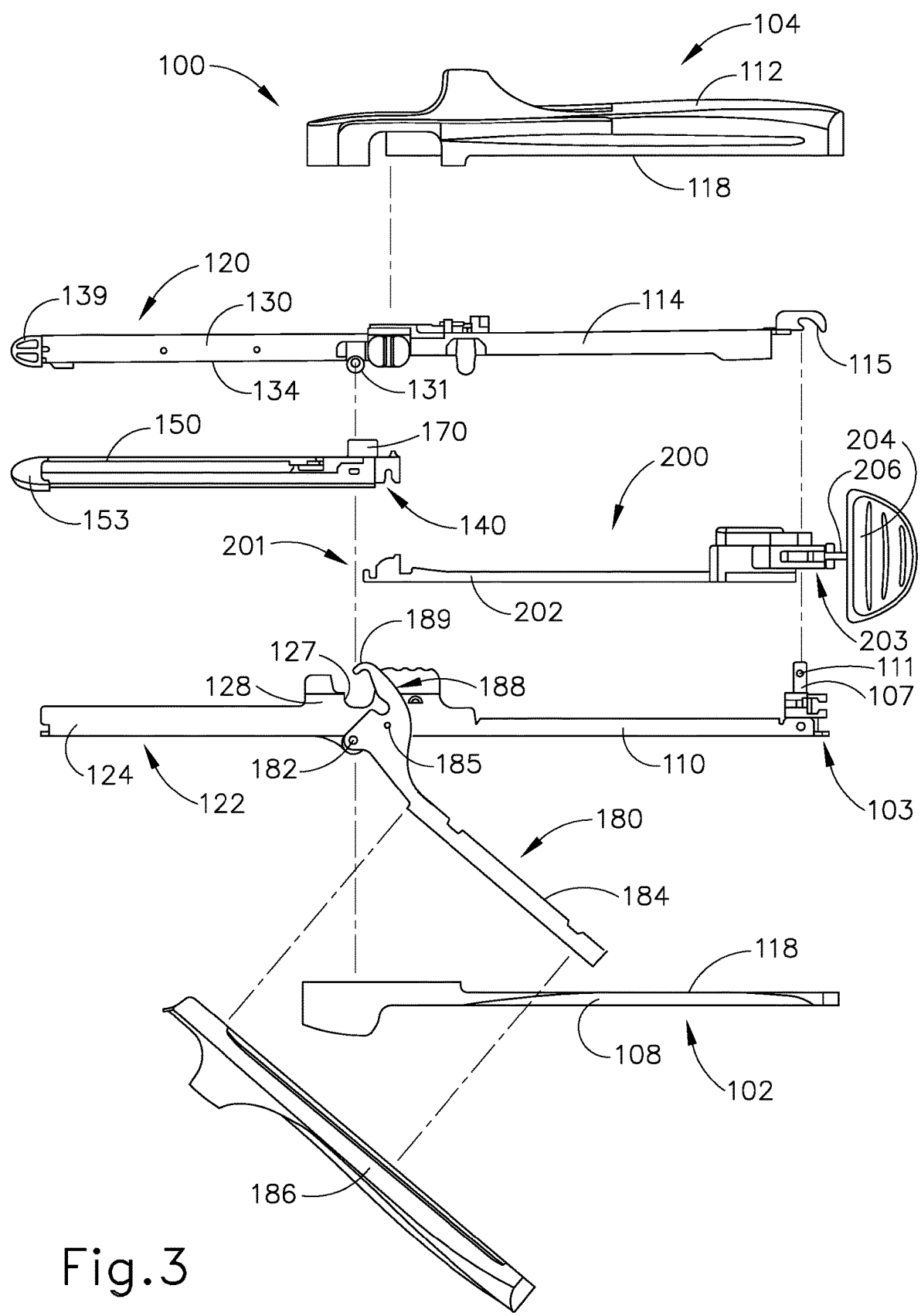
FIG. 3 depicts an exploded elevational side view of the surgical stapling instrument of FIG. 1.

As seen in FIG. 3, first portion (102) includes a first proximal frame (110), staple cartridge channel (122), and a latching lever (180). First proximal frame (110) extends from a proximal end (103) distally into staple cartridge channel (122). In the present example, first proximal frame (110) and staple cartridge channel (122) are formed integrally so as to define an elongate cartridge channel member having a unitary construction. Latching lever (180) is pivotably coupled to either staple cartridge channel (122) or first proximal frame (110) via a pin (182). First proximal frame (110) may be coupled with a handle cover (108) configured to promote sufficient grip such that an operator may control instrument (100) while the operator performs a suitable procedure. Handle cover (108) may couple with first proximal frame (110) by any suitable means as would be apparent to one having ordinary skill in the art in view of the teachings herein. Alternatively, handle cover (108) may be unitarily coupled with first proximal frame (110) or even omitted.

First proximal frame (110) defines a channel that slidably houses actuating beam (202) of firing assembly (200). Proximal end (103) includes one or more lateral pins, or projections (111). Projections (111) are configured to receive grooves (115) of second portion (104) in order to initially pivotably couple first and second portions (102, 104). In the current example, projections (111) are raised from the rest of first proximal frame (110) via a post (107), however this is merely optional. For instance, projections (111) may include a single pin extending laterally across side walls of first proximal frame (110). Of course, any suitable means of initially pivotably couplings first portion (102) and second portion (104) may be used as would be apparent to one having ordinary skill in the art in view of the teachings herein.

Figure 2:
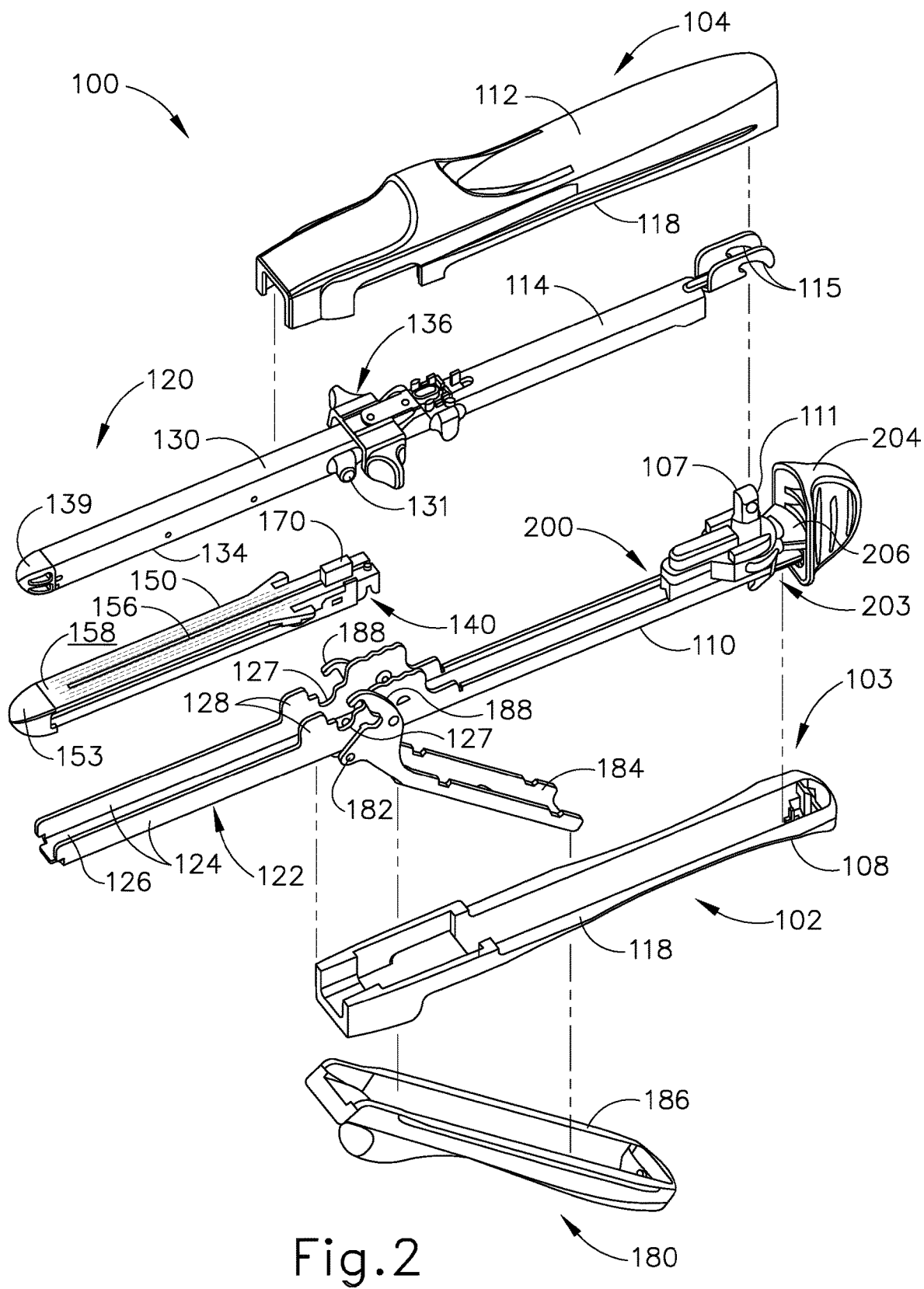
FIG. 2 depicts an exploded perspective view of the surgical stapling instrument of FIG. 1.
Figure 4:
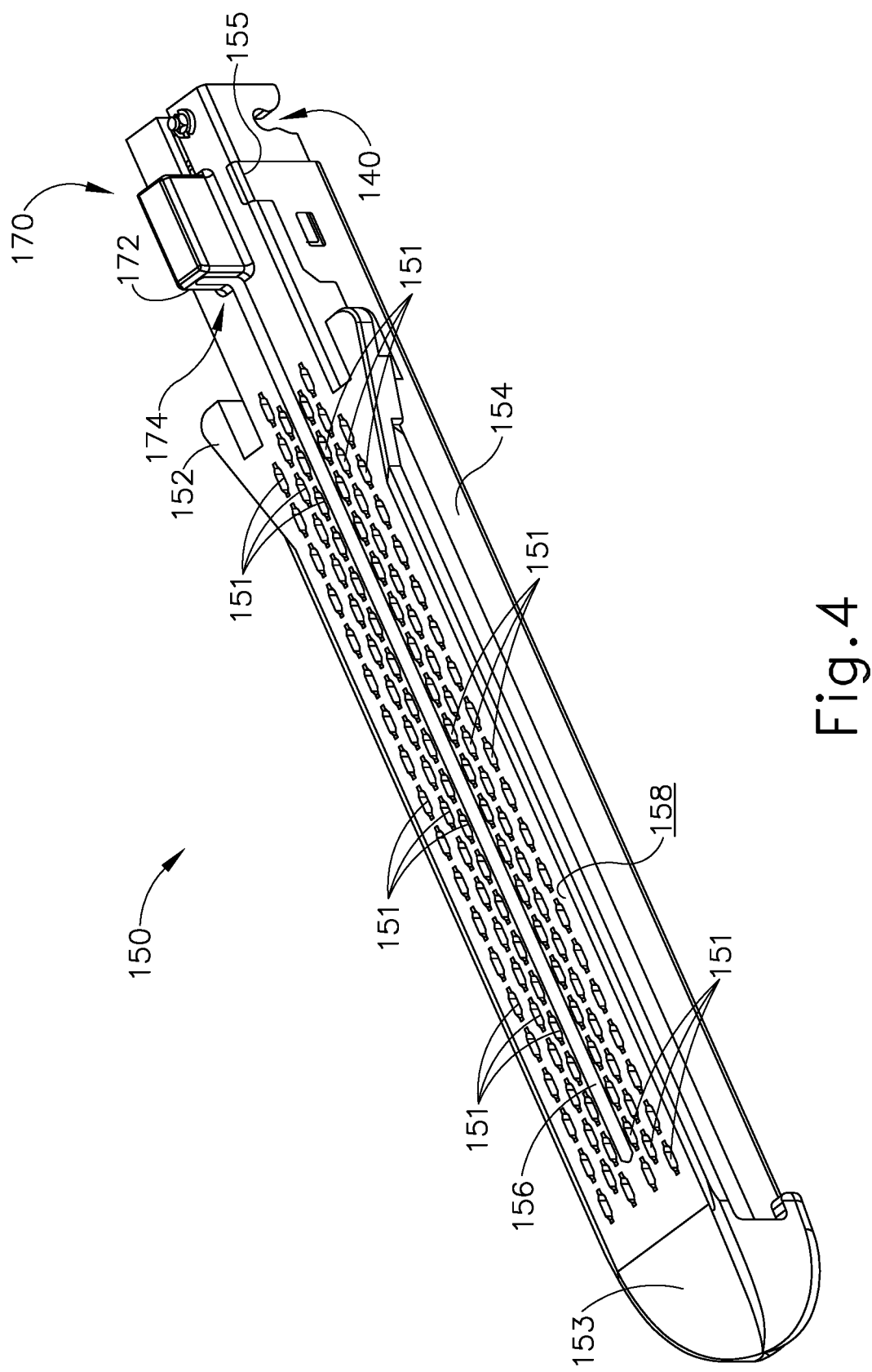
FIG. 4 depicts a perspective view of a staple cartridge assembly of the surgical stapling instrument of FIG. 1.

As briefly mentioned above, staple cartridge channel (122) extends distally from first proximal frame (110). As seen in FIG. 2, staple cartridge channel (122) is dimensioned to selectively couple and decouple with staple cartridge assembly (150). Staple cartridge channel (122) includes a bottom wall (126), and two opposed side walls (124) extending from opposite ends of bottom wall (126). Walls (124, 126) are dimensioned to receive at least a portion of staple cartridge assembly (150), as seen in FIG. 4. Additionally, side walls (124) include inwardly extending lateral projections (not shown) configured to receive coupling cutouts (140) defined by a proximal end of staple cartridge assembly (150). Coupling cutouts (140) may be dimensioned for a snap-fitting or press-fitting with inwardly extending lateral projections (not shown) of side walls (124) such that an operator may selectively attach and detach staple cartridge assembly (150) to staple cartridge channel (122). While coupling cutouts (140) and inwardly extending lateral projections (not shown) are used to selectively couple staple cartridge assembly (150) with staple cartridge channel (122), any other suitable coupling means may be used as would be apparent to one having ordinary skill in the art in view of the teachings herein. Side walls (124) of staple cartridge channel (122) also include side flanges (128) each defining a notch or recess (127). Recesses (127) are dimensioned to receive latch projections (131) of second portion (104) when second portion (104) pivots such that end effector (120) is in a fully closed position (as shown in FIG. 10D) relative to first portion (102).

As briefly mentioned above, latching lever (180) is pivotably coupled to the rest of first portion (102) via pivot pin (182). Latching lever (180) includes a proximal extending arm (184) and a distal latch body (188). Proximal extending arm (184) may be pivoted about pin (182) toward first proximal frame (110) in order to pivot distal latch body (188) toward staple cartridge channel (122) such that distal latch body (188) may engage and pivot second portion (104) toward first portion (102) to transition end effector (120) from a partially closed position (as shown in FIG. 10C) to a fully closed position (as shown in FIG. 10D).

Proximally extending arm (184) may be coupled with an arm cover (186) to promote sufficient grip such that an operator may grasp arm (184) while the operator performs a suitable procedure. Arm cover (186) may be coupled with proximal extending arm (184) by any suitable means as would be apparent to one having ordinary skill in the art in view of the teachings herein. Alternatively, arm cover (186) may be unitarily coupled with proximally extending arm (184) or even omitted.

Distal latch body (188) includes a pair of hooks (189). Distal latch body (188) also defines a corresponding pair of latch cutouts (185) located proximally relative to hooks (189). As will be described is greater detail below, each hook (189) is dimensioned to initially make contact with and then capture a respective latch projection (131) of second portion (104) such that distal latch body (188) may wrap around at least a portion of each latch projection (131) to further pivot second portion (104) toward first portion (102). As will also be described in greater detail below, each latch cutout (185) is dimensioned to receive a respective latch projection (131) when end effector (120) is in the closed position relative to first portion (102).

Figure 5:
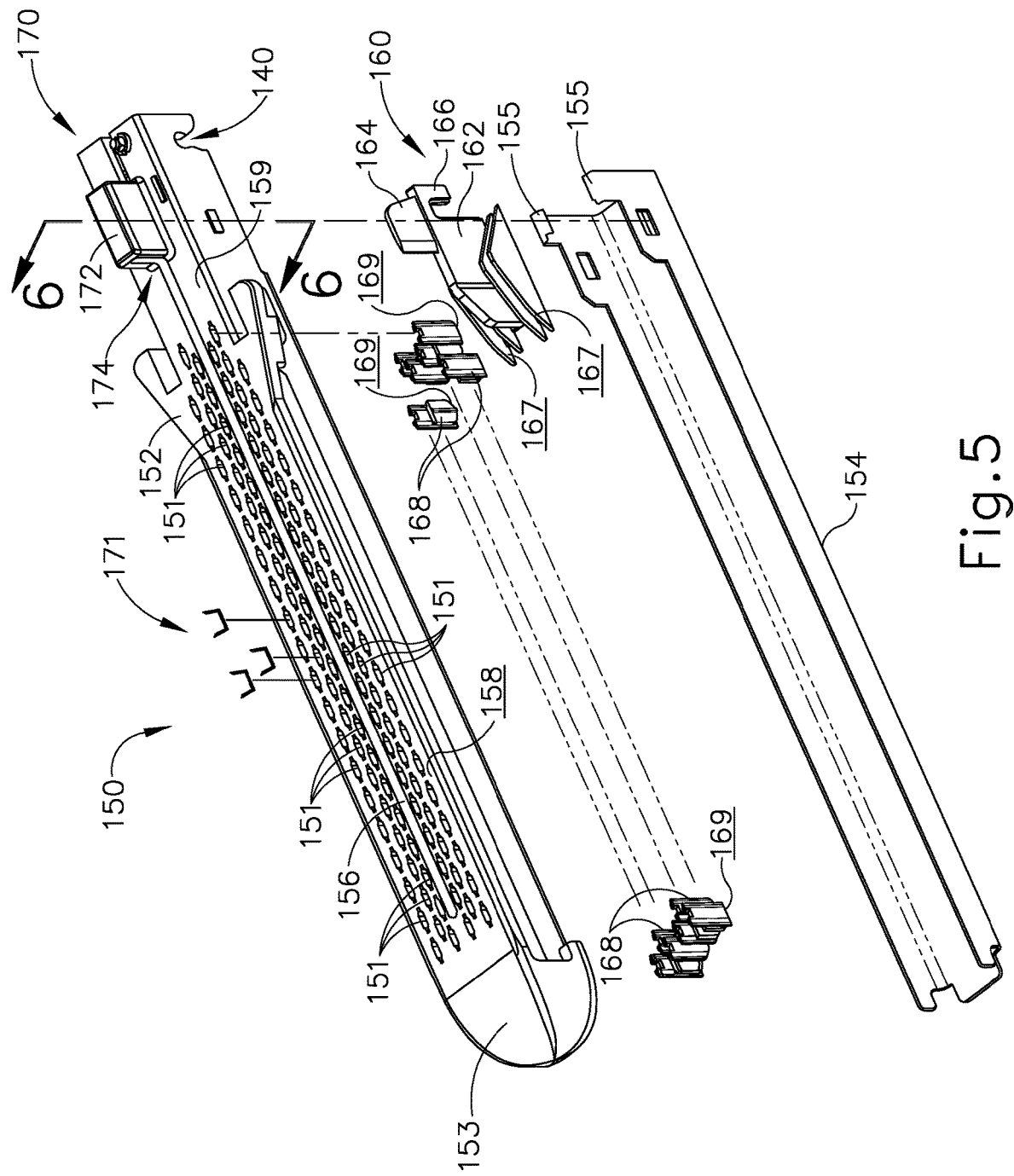
FIG. 5 depicts an exploded view of the staple cartridge assembly of FIG. 4.
Figure 6:
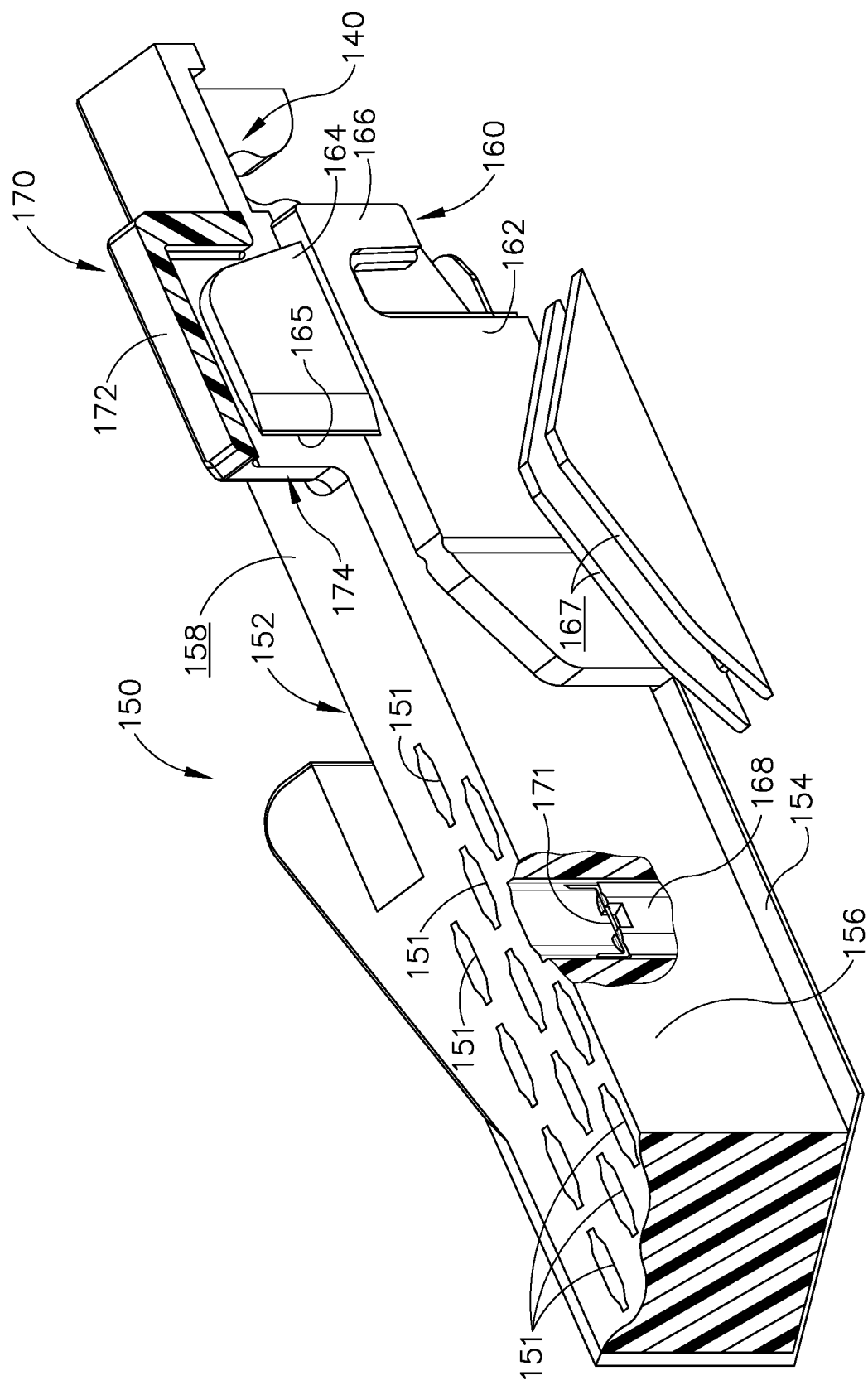
FIG. 6 depicts a cross-sectional perspective view of the staple cartridge assembly of FIG. 4, taken along line 6-6 of FIG. 5.

As best seen in FIGS. 4-6, staple cartridge assembly (150) includes a cartridge body (152), a pan (154), and a plurality of staple drivers (168), each configured to drive a respective staple (not shown). Cartridge body (152) defines a plurality of staple cavities (151), a slot (156), and coupling cutouts (140). Staple drivers (168) and respective staples (not shown) are slidably housed within a corresponding staple cavity (151). When first portion (102) and second portion (104) are coupled together, staple cartridge assembly (150) and staple cartridge channel (122) form a portion of end effector (120). As will be described in greater detail below, staple cartridge assembly (150) is configured to house or receive staple sled assembly (160) of firing assembly (200) such that staple sled assembly (160) may actuate through cartridge assembly (150) in order to simultaneously sever and staple tissue captured between the two halves of end effector (120).

As mentioned above, coupling cutouts (140) of cartridge body (152) may be dimensioned for a snap-fitting with inwardly extending lateral projections (not shown) of side walls (124) of staple cartridge channel (122) such that an operator may selectively attach and detach staple cartridge assembly (150) to staple cartridge channel (122). Cartridge body (152) includes a distal nose (153). When staple cartridge assembly (150) is properly coupled with cartridge channel (122), distal nose (153) may extend distally from cartridge channel (122) to provide an atraumatic tip.

Additionally, cartridge body (152) includes a staple deck (158). Staple deck (158) partially defines staple cavities (151) such that staple cavities (151) extend from an interior of cartridge body (152) toward an open end at staple deck (158). Staple cavities (151) each house a corresponding staple driver (168) and staple (not shown). Similarly, staple deck (158) partially defines slot (156) that extends from an interior of cartridge body (152) toward an open end at staple deck (158). Slot (156) is dimensioned to slidably receive a portion of a sled body (162) and cutting member (164) of staple sled assembly (160) such that cutting member (164) may sever tissue as staple sled assembly (160) slides distally through cartridge body (152).

Pan (154) may include flexible arms (155). Flexible arms (155) may be configured to engage cartridge body (152) such that pan (154) may couple with cartridge body (152) in a snap-fit or press-fit relationship. Pan (154) may couple with cartridge body (152) after staple drivers (168) and staples (not shown) have been inserted into respective staple cavities (151). Pan (154) may therefore act as a floor for staple drivers (168).

In the current example, cartridge body (152) includes a sled assembly housing (170) located near the proximal end of staple cartridge assembly (150). Sled assembly housing (170) is configured to initially house staple sled assembly (160) of firing assembly (200). Sled assembly housing (170) includes a body (172) defining a cavity (174) having a distally facing opening. Body (172) and cavity (174) are dimensioned to house a cutting member (164) of sled assembly (160) prior to firing, therefore acting as a sheath for cutting member (164). When fired, cutting member (164) may exit sled assembly housing (170) via the distally facing opening of cavity (174).

As seen best in FIGS. 7 and 8, sled assembly (160) includes a sled body (162) and a cutting member (164). Cutting member (164) includes a cutting edge (165) and a lock arm (166). Sled body (162) defines a cutout (161) and a slot (163). Slot (163) is dimensioned to receive a portion of cutting member (164) such that cutting member (164) and sled body (162) may actuate together. Cutting member (164) may couple with sled body (162) via an inference fit with slot (163), through use of adhesives, or any other suitable manner was would be apparent to one having ordinary skill in the art in view of the teachings herein. Alternatively, cutting member (164) may couple with sled body (162) though any suitable manner as would be apparent to one having ordinary skill in the art in view of the teachings herein, such as being unitarily connected, welding, etc. Cutout (161) is dimensioned to couple with distal end (201) of actuating beam (202) when staple cartridge assembly (150) is properly attached to staple cartridge channel (122). Therefore, when properly coupled, actuating beam (202) may drive sled assembly (160) longitudinally through cartridge body (152). It should be understood that since actuating beam (202) is coupled with sled assembly (160) during exemplary use, actuating beam (202) is also dimensioned to slide within slot (156) defined by cartridge body (152).

Sled body (162) also includes a plurality of cam surfaces (167) dimensioned to slide longitudinally within respective elongate grooves (not shown) that pass through staple cavities (151) of cartridge body (152). In particular, cam surfaces (167) are configured to engage and cam against sloped surfaces (169) of staple drivers (168) within staple cavities (151) in order to actuate staple drivers (168) toward staple deck (158). Staple drivers (168) then drive corresponding staples (not shown) through staple cavities (151) away from staple deck (158).

As mentioned above, staple sled assembly (160) is configured to couple with the rest of firing assembly (200) when staple cartridge assembly (150) is suitably coupled with staple cartridge channel (122). In the current example, staple sled assembly (160) of firing assembly (200) is associated with cartridge assembly (150) such that after cartridge assembly (150) is used and disposed of, so is staple sled assembly (160). Therefore, when an additional cartridge assembly (150) is loaded into staple cartridge channel (122), a new staple sled assembly (160) will be present. However, this is merely optional. For instance, staple sled assembly (160) may be fixed or otherwise coupled to the rest of firing assembly (200) such that the same staple sled assembly (160) may be used multiple times with multiple staple cartridge assemblies (150). In such examples, cartridge body (152) would not need a sled assembly housing (170). Various ways in which staple sled assembly (160) may be incorporated into either staple cartridge assembly (150), staple cartridge channel (122), or first proximal frame (110) will be apparent to one having ordinary skill in the art in view of the teachings herein.

As shown in FIGS. 2 and 3, second portion (104) of instrument (100) includes a second proximal frame (114), anvil channel (130), latch projections (131), and an anvil plate (134). Second proximal frame (114) extends from a proximal end defining grooves (115) in anvil channel (130). In the present example, second proximal frame (114) and anvil channel (130) are formed integrally so as to define an elongate anvil channel member having a unitary construction. Second proximal frame (114) may be coupled with a handle cover (112) configured to promote sufficient grip such that an operator may control instrument (100) while the operator performs a suitable procedure. Handle cover (112) and second proximal frame (114) may couple with each other by any suitable means as would be apparent to one having ordinary skill in the art in view of the teachings herein. Alternatively, handle cover (112) may be unitarily coupled with second proximal frame (114) or even omitted. Second proximal frame (114) may also define a channel configured to enable portions of firing assembly (200) to actuate relative to first portion (102) and second portion (104) when end effector (120) is in the fully closed position (as shown in FIG. 10D).

Figure 9:
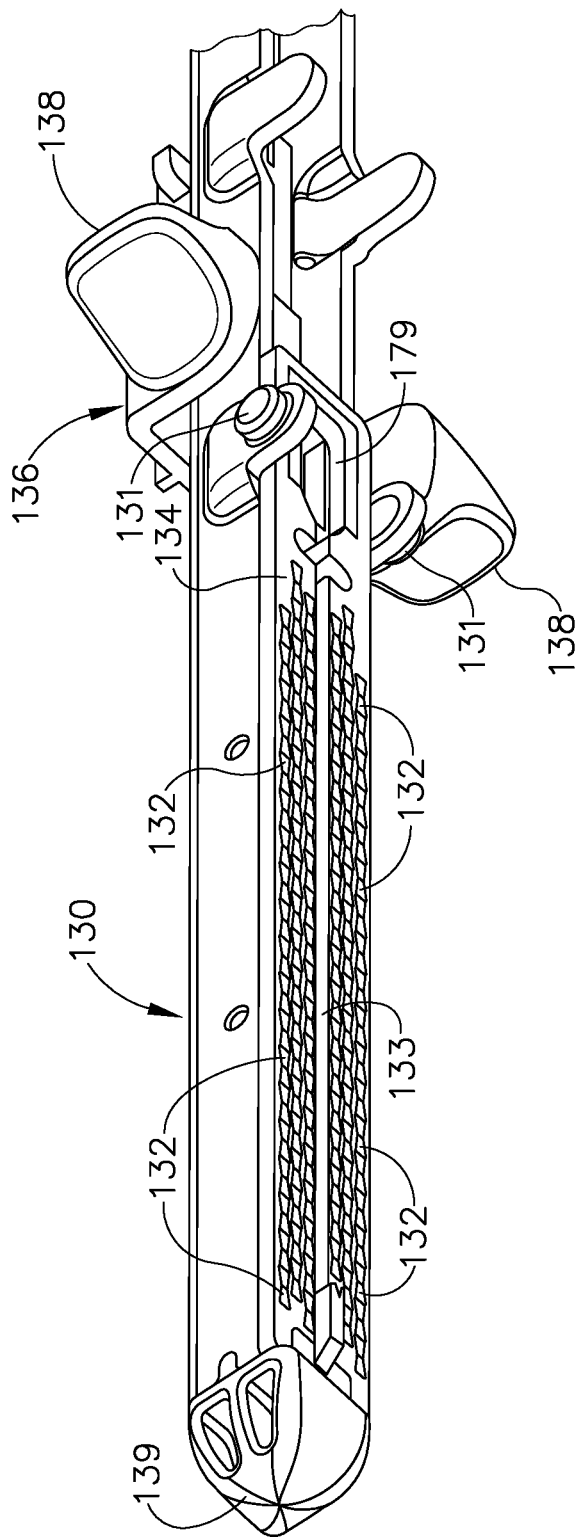
FIG. 9 depicts a perspective view of an anvil assembly of the surgical stapling instrument of FIG. 1.

Second portion (104) terminates distally in a distal nose (139). Distal nose (139) may extend distally from anvil channel (130) to provide an atraumatic tip. As shown in FIG. 9, proximal end of anvil plate (134) defines a recess (179) dimensioned to receive sled assembly housing (170) when first portion (102) and second portion (104) are pivoted toward each other. As will be described in greater detail below, latch projections (131) extend laterally away from anvil channel (130) and are dimensioned to interact with distal latch body (180) to draw anvil plate (134) toward staple cartridge assembly (150).

Anvil plate (134) defines a plurality of staple forming pockets (132) and a slot (133). Staple forming pockets (132) are positioned along anvil plate (134) such that each staple forming pocket (132) aligns with a corresponding staple cavity (151) when anvil channel (130) is pivoted toward staple cartridge channel (122) to the fully closed position (as shown in FIGS. 1, 10D, and 11A-B). Therefore, when cam surfaces (167) of sled body (162) actuate staple drivers (168) in accordance with the description above, staples (not shown) are driven through staple cavities (151) away from staple deck (158), through tissue, and against a corresponding staple forming pocket (132) such that staples (not shown) transform from a general "U" shape into a general "B" shape in order to suitably staple tissue. Slot (133) is dimensioned to laterally align with slot (156) of staple cartridge assembly (150) when anvil channel (130) is pivoted to the fully closed position (as shown in FIGS. 1, 10D, 11A-11B). Slot (133) is dimensioned to slidably receive a portion of cutting member (164) as staple sled assembly (160) is driven through staple cartridge assembly (150) such that cutting member (164) may sever tissue captured between anvil surface (134) and staple deck (158) during exemplary use.

As seen best in FIG. 9, second portion (104) of instrument (100) of the present example further includes a staple height adjustment mechanism (136). Adjustment mechanism (136) is operatively coupled with anvil plate (134), for example via one or more camming features (not shown), and includes a pair of user-engageable projections (138). Adjustment mechanism (136) is selectively movable relative to anvil channel (130) between two or more longitudinal positions to raise or lower anvil plate (134) relative to anvil channel (130), and thereby adjust a gap distance (or "tissue gap") between anvil plate (134) and staple deck (158) when first and second instrument portions (102, 104) are coupled together in a fully closed position. A larger gap distance, and thus a greater staple height, may be provided for stapling tissues of greater thicknesses. Similarly, a smaller gap distance, and thus a smaller staple height, may be provided for stapling tissues of lesser thicknesses. It will be appreciated that staple height adjustment mechanism (136) is merely optional and may be omitted in other examples.

Surgical linear cutting stapler (100) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and U.S. Pat. No. 8,789,740, entitled "Linear Cutting and Stapling Device with Selectively Disengageable Cutting Member," issued Jul. 29, 2014. The disclosure of each of these references is incorporated by reference herein.

Figure 10A:
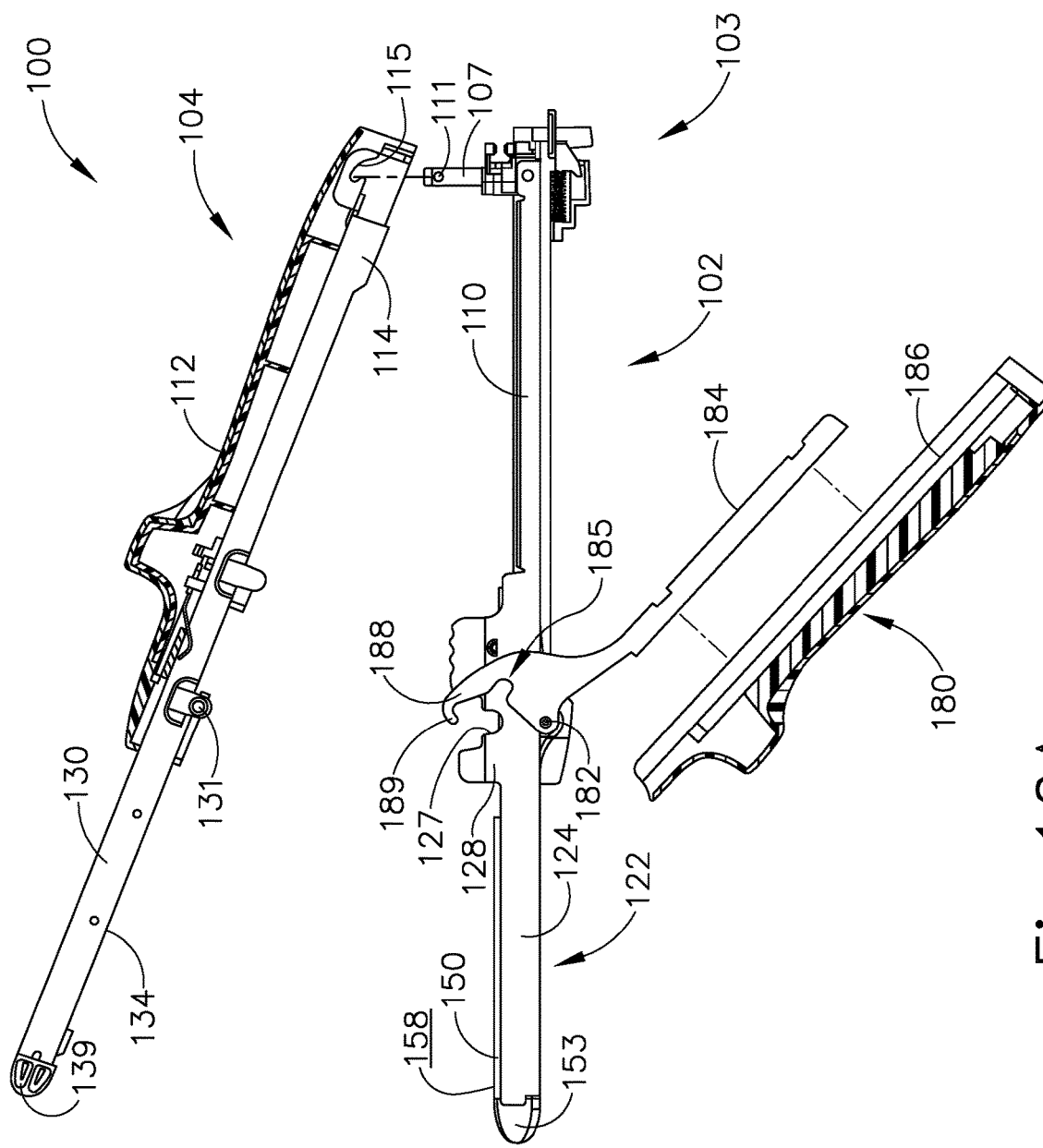
FIG. 10A depicts a cross-sectional side view of the surgical stapling instrument of FIG. 1, where a first portion and a second portion are decoupled from each other, and where an arm cover of the second portion is shown detached from the first portion for illustrative purposes.
Figure 10B:
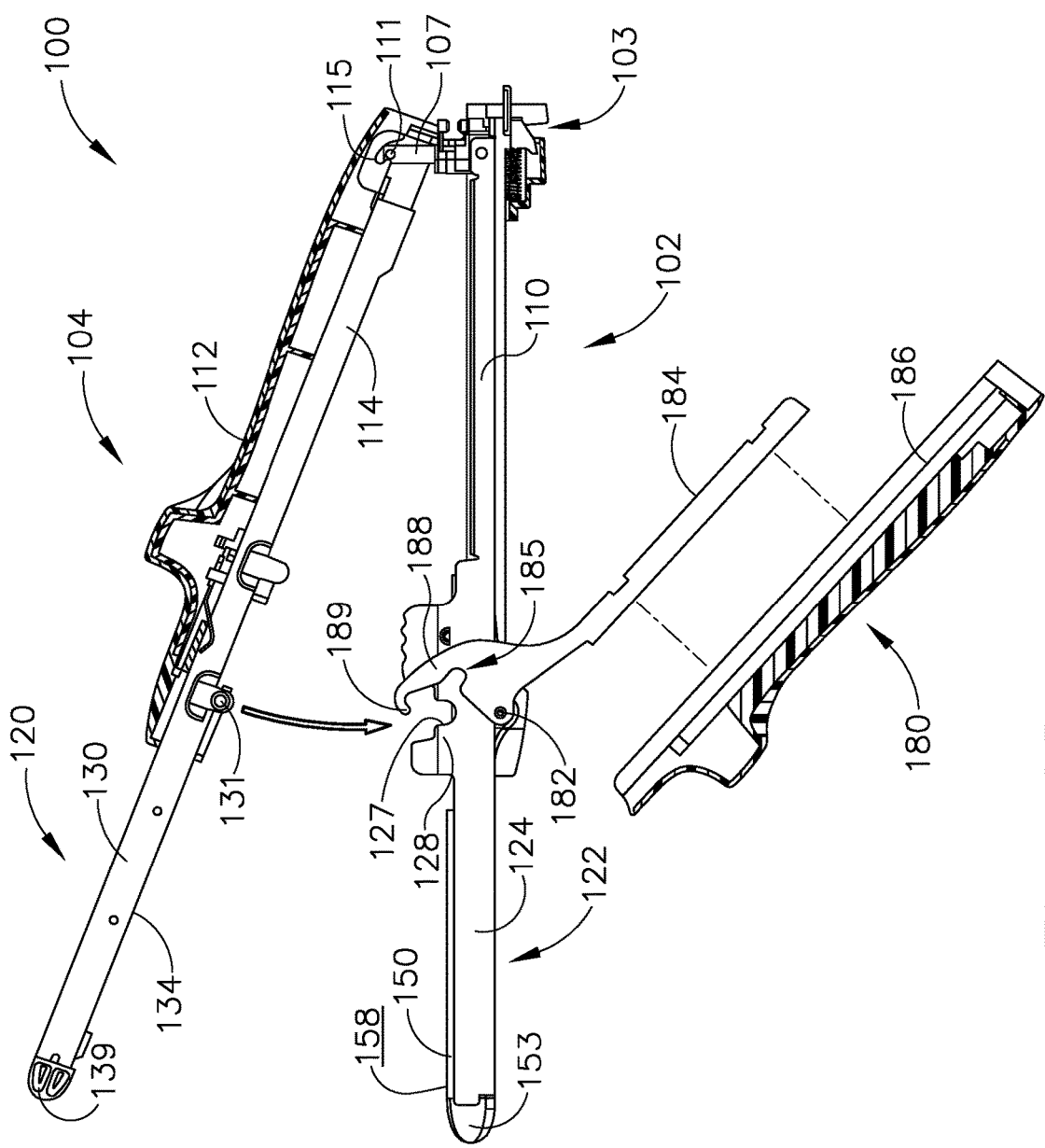
FIG. 10B depicts a cross-sectional side view of the surgical instrument of FIG. 1, where the first portion and the second portion of FIG. 10A are coupled with each other in an opened position.
Figure 10C:
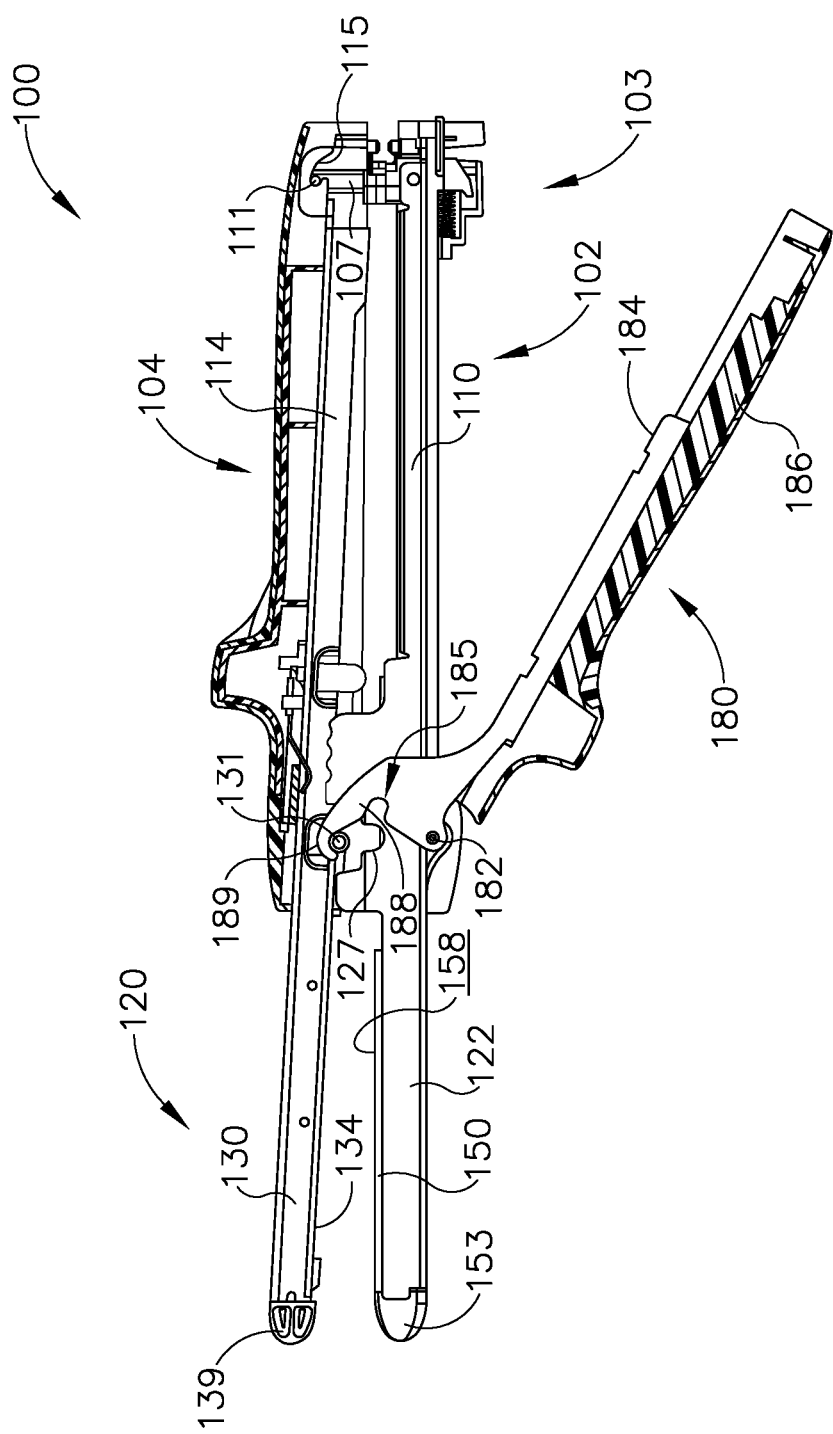
FIG. 10C depicts a cross-sectional side view of the surgical instrument of FIG. 1, where the first portion and the second portion of FIG. 10A are coupled with each other in a partially closed position.
Figure 10D:
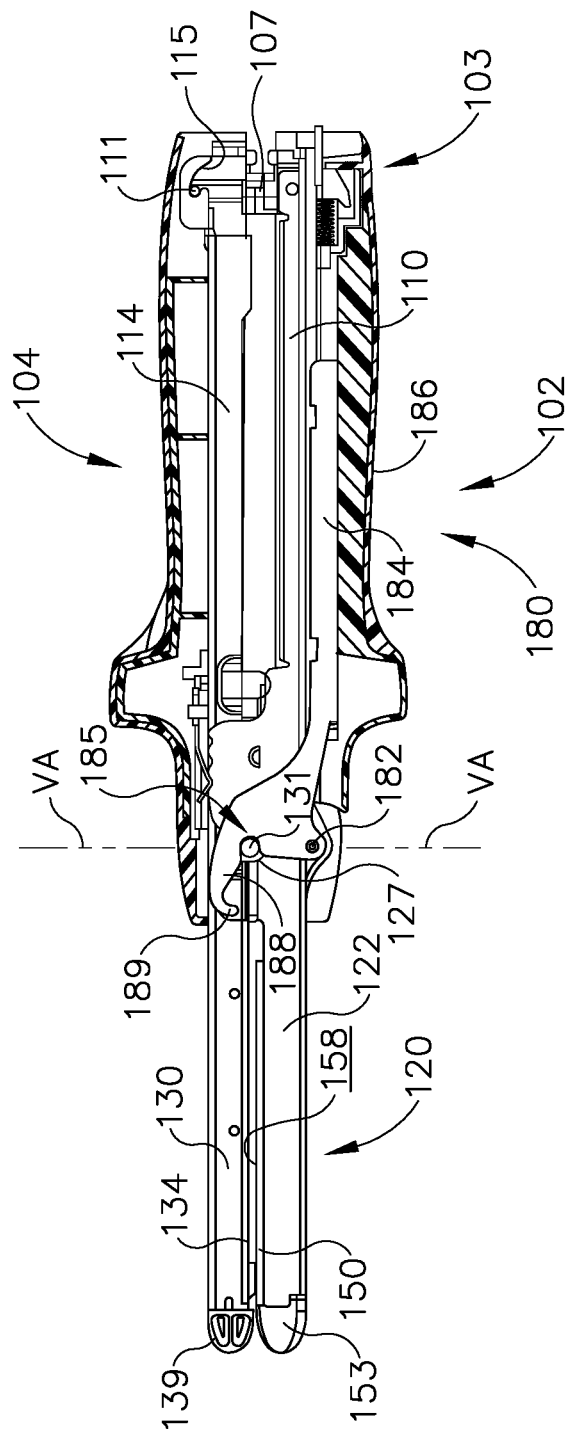
FIG. 10D depicts a cross-sectional side view of the surgical instrument of FIG. 1, where the first portion and the second portion of FIG. 10A are coupled with each other in a fully closed position.
Figure 11A:
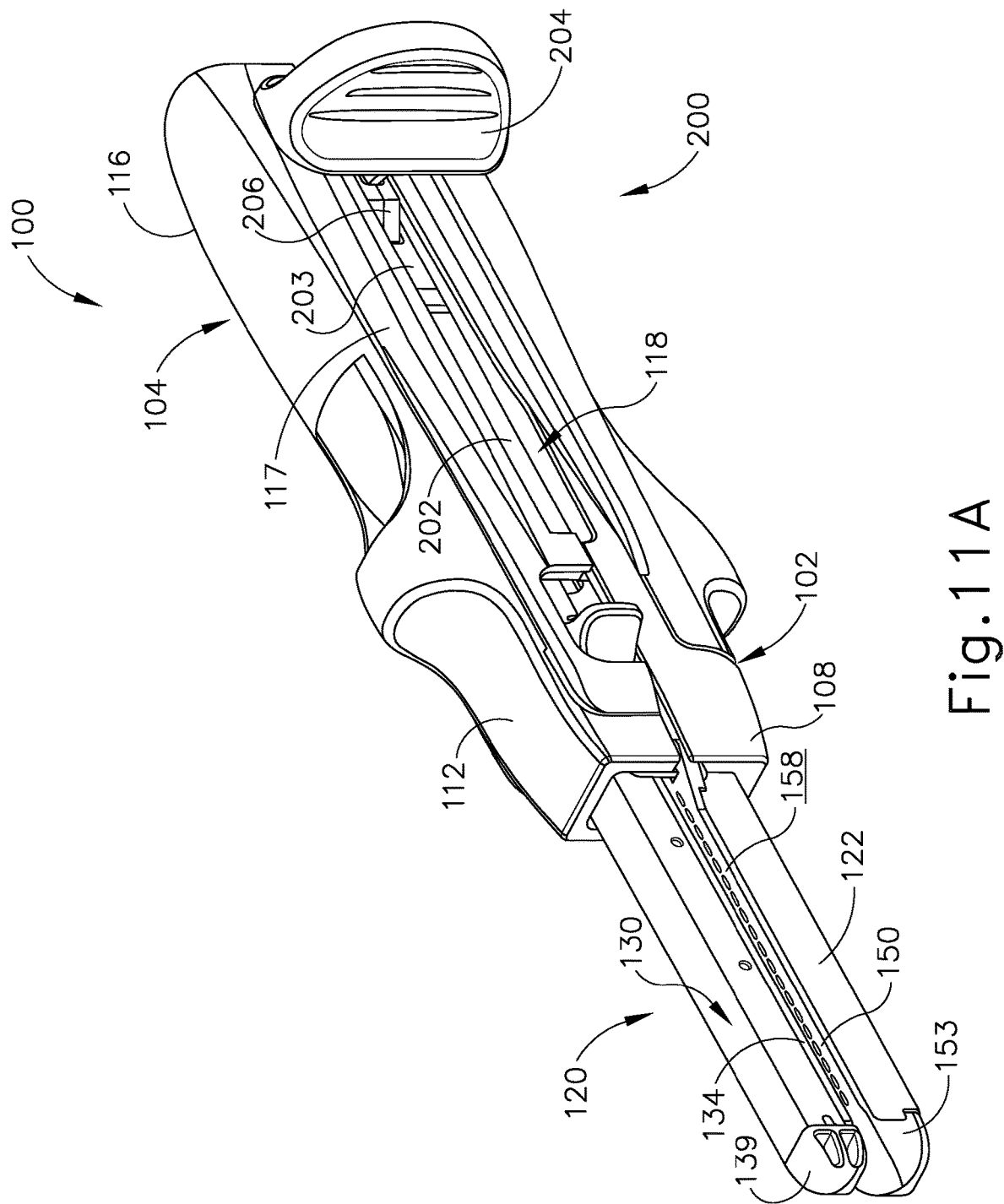
FIG. 11A depicts a perspective view of the surgical instrument of FIG. 1, where a firing assembly is in a pre-fired position.
Figure 11B:
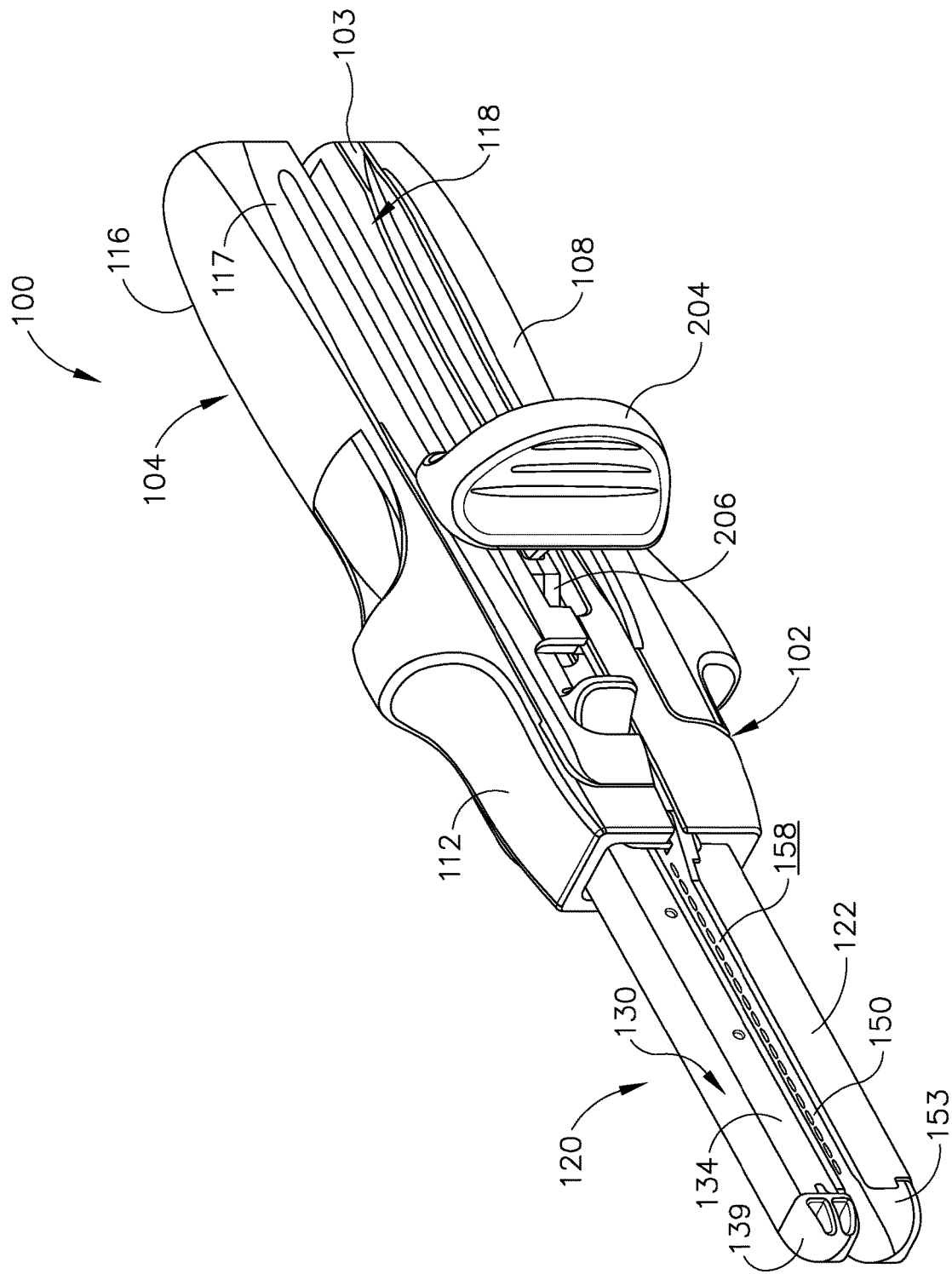
FIG. 11B depicts a perspective view of the surgical instrument of FIG. 1, where the firing assembly of FIG. 11A is in a fired position.

FIGS. 10A-11B show an exemplary use of instrument (100). In particular, FIGS. 10A-10D show an exemplary coupling of first portion (102) with second portion (104), and pivoting first portion (102) and second portion (104) such that end effector (120) transitions from an open position (FIG. 10B), to a partially closed position (FIG. 10C), and finally to a fully closed position (FIG. 10D). FIGS. 11A-11B show an exemplary firing of instrument (100) when end effector (120) is in a fully closed position.

FIG. 10A shows first portion (102) completely detached from second portion (204). Additionally, staple cartridge assembly (150) is suitably attached to staple cartridge channel (122) in accordance with the description above. At this point during a procedure, such as during a gastrointestinal anastomosis, an operator may desire to place lumens of tissue over and past distal noses (139, 153) of second portion (104) and cartridge assembly (150), respectively, such that lumens of tissue are suitably associated with both anvil plate (134) and cartridge assembly (150). At this point, an operator may align grooves (115) of second portion (104) with corresponding lateral projections (111) of first portion (102) in preparation of initially pivotally coupling first portion (102) with second portion (104).

Next, as shown in FIG. 10B, an operator may insert lateral projections (111) into corresponding grooves (115) such that first portion (102) and second portion (104) are pivotally coupled, but end effector (120) is in an open position. First portion (102) and second portion (104) may pivot relative to each other about the axis defined by lateral projections (111). At this point, latching lever (180) is not in contact with any portion of second portion (104). Additionally, latching lever (180) is in an open position such that proximal extending arm (184) is pivoted away from first proximal frame (110).

Next, as shown in FIG. 10C, an operator may initially pivot anvil channel (130) and anvil plate (134) toward cartridge channel (122) and staple cartridge assembly (150), and partially pivot latching lever (180) such that hooks (189) initially contact latch projections (131). At this point, end effector (120) is in the partially closed position. As best shown between FIGS. 10C-10D, after hooks (189) initially contact latch projections (131), an operator may further rotate proximal extending arm (184) toward first proximal frame (110), causing distal latch body (188) to drive latch projections (131) along the surfaces of distal latch body (188) toward latch cutouts (185). As latch projections (131) are driven toward latch cutouts (185), anvil channel (130) and anvil plate (134) rotate further toward cartridge channel (122) and staple cartridge assembly (150) such that end effector (120) is in the closed position. Additionally, latch projections (131) are also driven toward recesses (127) of staple cartridge channel (122) such that each latch projection (131) is encompassed by a combination of the respective latch cutout (185) and recess (127), effectively latching end effector (120) into the closed position. Latch cutouts (185) and recesses (127) may be dimensioned to interface with latch projections (131) while end effector (120) is in the fully closed position such that latch projections (131) and pivot pin (182) extend along a vertical axis (VA) that is substantially perpendicular with the longitudinal axis of instrument (100). This may provide a mechanical advantage for an enhanced closure force during suitable use.

FIGS. 11A-11B show an exemplary firing of instrument (100) with end effector (120) in the fully closed position. As best seen in FIG. 11A, an operator may pivot actuator (204) to either side (116, 117) of instrument (100). In the present example, actuator (204) has been pivoted to second side (117) of instrument (100). Next, operator may push actuator (204) distally toward end effector (120) within slot (118), such that actuating beam (202) and sled (160) are fired, thereby stapling and severing tissue captured between stapling deck (158) and anvil plate (134) in accordance with the description above. Once instrument (100) has been fired, an operator may pull actuator (204) proximally back to the position shown in FIG. 11A, then rotate actuator (204) back to the position shown in FIG. 1. An operator may then pivot latching lever (180) such that proximally extending arm (184) is pivoted away from first proximal frame (110) in order to open end effector (120) from the fully closed position to the partially closed position. An operator may further pivot latching lever (180) such that distal latch body (188) no longer captures latch projections (131). Then an operator may decouple first portion (102) and second portion (104) from each other and replace staple cartridge assembly (150), if desired.

II. Exemplary Linear Cutting Staplers Having Release Assemblies

As described above, an operator may pivot latching lever (180) about pin (182) in a first direction in order to pivot end effector (120) from a partially closed position (as shown in FIG. 10C) to a fully closed position (as shown in FIG. 10D). As also described above, an operator may also pivot latching lever (180) about pin (182) in a second, opposite, direction in order to open end effector (120) from the fully closed position (as shown in FIG. 10D) back to the partially closed position (as shown in FIG. 10C).

In some instances, once end effector (120) is pivoted to the fully closed position, it may be difficult to open end effector (120) by directly grasping proximal extending arm (184) to pivot latching lever (180). End effector (120) may lock-up in the fully closed position such that it requires a great amount of force to initially pivot latching lever (180) out of the fully closed position. Such difficulty may be increased when latch projections (131) and pivot pin (182) are dimensioned to extend along a common vertical axis (VA) thereby providing a mechanical advantage for enhanced closure force as described above. Therefore, it may be desirable to provide a release assembly that may help urge latching lever (180) to initially pivot end effector (120) out of the fully closed position such that an operator may then more easily open end effector (120) by directly grasping and rotating proximal extending arm (184) afterwards. Examples of alternative release assemblies are described in greater detail below.

A. Exemplary Instrument with First Release Assembly

FIGS. 12A-12D show an exemplary alternative instrument (300) that may be used in place of instrument (100) described above. Instrument (300) is substantially similar to instrument (100) described above, with differences elaborated below. Instrument (300) includes a first portion (302) having a staple cartridge channel (322), a second portion (304) having an anvil channel (330), a staple cartridge assembly (350) that may selectively couple with cartridge channel (322) of first portion (302), a firing assembly (390), and a release assembly (360).

First portion (302), second portion (304), staple cartridge assembly (350), and firing assembly (390) are substantially similar to first portion (102), second portion (104), staple cartridge assembly (150), and firing assembly (200) described above, respectively, with difference described below. Therefore, first portion (302) and staple cartridge assembly (350) may pivotably couple with second portion (304) to form an end effector (320) that is capable of clamping, severing, and stapling tissue captured between opposing halves of end effector (320). As will be described in greater detail below, release assembly (360) is configured to help urge latching lever (380) to initially pivot end effector (320) out of the fully closed position toward a partially closed position.

Firing assembly (390) includes an actuating beam (392), an actuator (394), and a staple sled assembly (not shown), substantially similar to actuating beam (202), actuator (204), and staple sled assembly (160) described above, respectively, with differences described below. In the current example, actuator (394) may not pivot to either lateral side of instrument (300). However, this is merely optional, as actuator (394) may be configured substantially similar to actuator (204) described above; or similar to any other actuator that would be apparent to one having ordinary skill in the art in view of the teachings herein.

First portion (302) includes a first proximal frame (310), staple cartridge channel (322), and a latching lever (380), which are substantially similar to first proximal frame (110), staple cartridge channel (122), and latching lever (180), described above, respectively, with differences elaborated below. In the present example, first proximal frame (310) and staple cartridge channel (322) are formed integrally so as to define an elongate cartridge channel member having a unitary construction. Latching lever (380) is pivotably coupled to either staple cartridge channel (322) or first proximal frame (310) via a pin (382).

First proximal frame (310) defines a channel that slidably houses actuating beam (392) of firing assembly (390). While first proximal frame (110) of instrument (100) includes one or more lateral pins, or projections (111) that are configured to be received in groove (115) of second portion (104); first proximal frame (310) of the current example defines grooves (315) that are configured to house lateral pins or projections (311) of second portion (304). Grooves (315) are configured to house pins (311) of second portion (304) in order to initially pivotably couple first and second portions (302, 304). Rather than both first portion (102) and second portion (104) defining lateral slot (118) while end effector (120) is in the fully closed position; first portion (302) of the current example defines lateral slot (318) alone, which defines a pathway for actuator (394) to travel.

Similar to staple cartridge channel (122) and staple cartridge assembly (150) described above, staple cartridge channel (322) is dimensioned to selectively couple and decouple with staple cartridge assembly (350). Cartridge assembly (350) includes a staple deck (358) and a distal nose (353) which are substantially similar to staple deck (158) and distal nose (153) described above. Staple cartridge channel (322) also defines notches or recesses (327) which are substantially similar to notches or recesses (127) described above. Therefore, recesses (327) are dimensioned to receive latch projections (331) of second portion (304) when second portion (304) pivots such that end effector (320) is in a fully closed position (as shown in FIGS. 12B-12C) relative to first portion (302).

Latching lever (380) includes a proximal extending arm (384) and a distal latch body (388), which are substantially similar to proximal extending arm (184) and distal latch body (188) described above, respectively. Therefore, distal latch body (388) includes a pair of hooks (389) which are substantially similar to hooks (189) described above. Additionally, distal latch body (388) also defines a corresponding pair of latch cutouts (385), which are substantially similar to latch cutouts (185) described above.

Second portion (304) of instrument (300) includes a second proximal frame (314), anvil channel (330), latch projections (331), and an anvil plate (334), which are substantially similar to second proximal frame (114), anvil channel (130), latch projections (131) and anvil plate (134) describe above, with differences described herein. Second portion (304) terminates distally in a distal nose (339), which extends distally from anvil channel (330) to provide an atraumatic tip.

As mentioned above, and as will be described in greater detail below, release assembly (360) is configured to help urge latching lever (380) to initially pivot end effector (320) out of a fully closed position toward a partially closed position. Release assembly (360) includes a rotating body (364) pivotably coupled to first proximal frame (310) via a pivot pin (362). Therefore, rotating body (364) may rotate relative to proximal frame (310) about an axis defined by pivot pin (362). Rotating body (364) includes a first leg (366) and a second leg (368). First leg (366) is dimensioned to abut against actuator (394) as actuator (394) travels toward a proximal position along the path defined by lateral slot (318). Second leg (368) is dimensioned to abut against proximal extending arm (384) without interfering with translation of actuator (394). Second leg (368) may be partially housed within the channel defined by first proximal frame (310) or any other suitable location at would be apparent to one having ordinary skill in the art in view of the teachings herein. As will be described in greater detail below, rotating body (364) is configured to pivot in response to proximal translation of actuator (394), thereby initially urging latching lever (380) to pivot such that end effector (320) transitions from the fully closed position toward the partially closed position. Afterwards, an operator may more easily open end effector (320) by directly grasping and rotating proximal extending arm (384).

Figure 12A:
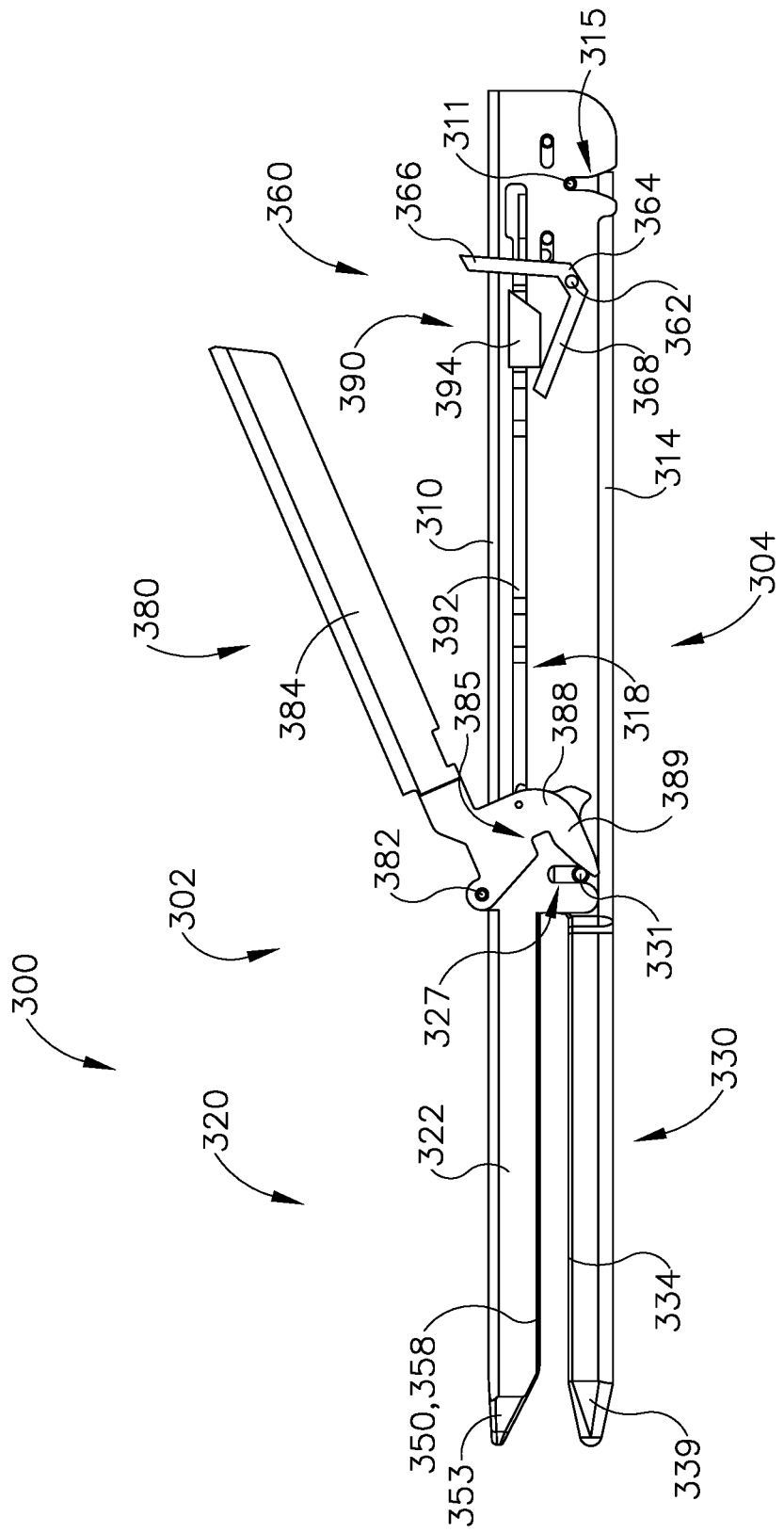
FIG. 12A depicts a side elevation view of an alternative surgical instrument having a first portion, a second portion, a firing assembly, and a release assembly, where the first portion is coupled with the second portion in a partially closed position, where the firing assembly is in an unfired position, and where the release assembly is in a first position.
Figure 12B:
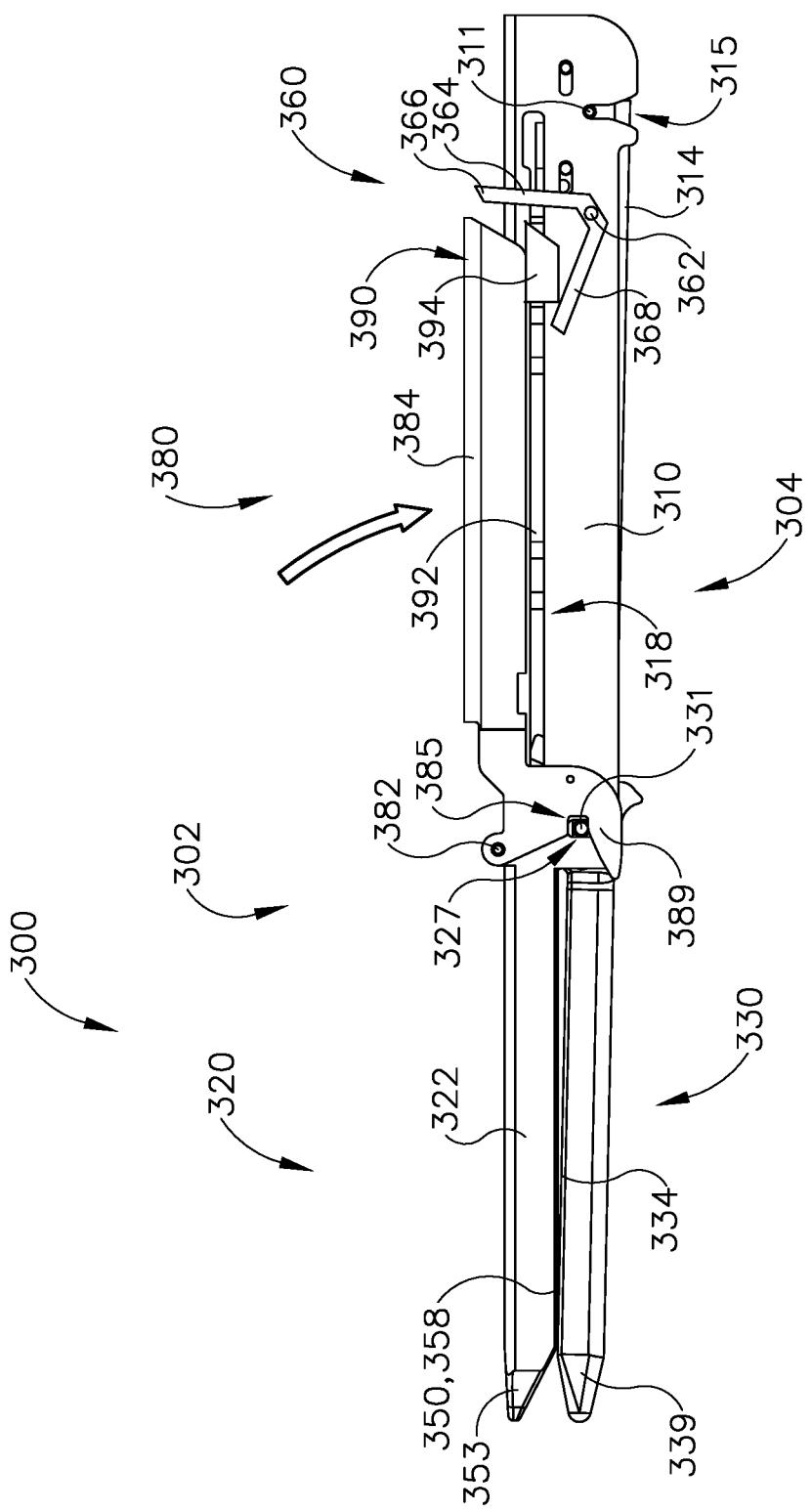
FIG. 12B depicts a side elevation view of the surgical instrument of FIG. 12A, where the first portion is coupled with the second portion in a fully closed position, where the firing assembly is in the unfired position, and where the release assembly is in the first position.
Figure 12C:
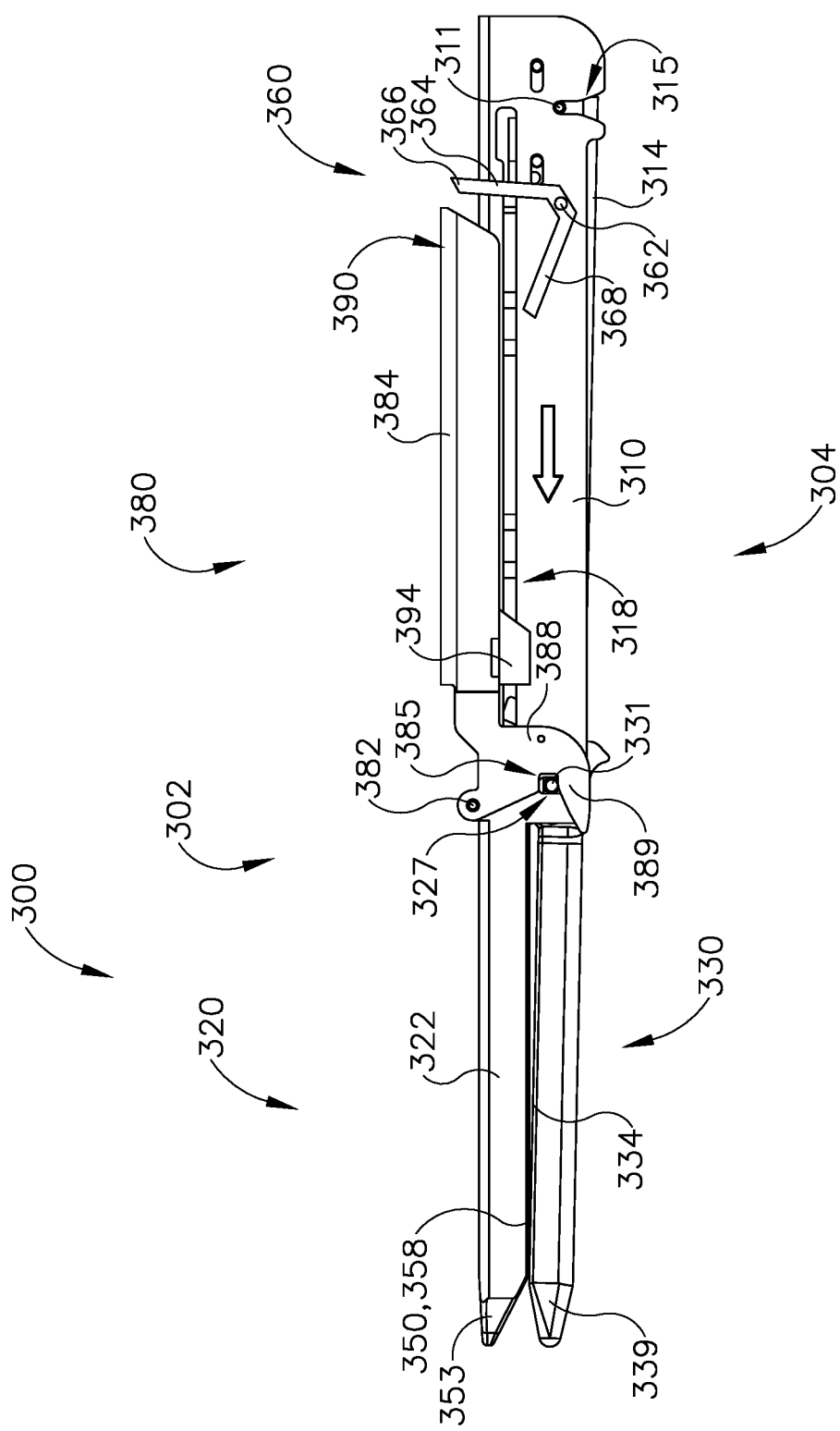
FIG. 12C depicts a side elevation view of the surgical instrument of FIG. 12A, where the first portion is coupled with the second portion in the fully closed position, where the firing assembly is in a fired position, and where the release assembly is in the first position.
Figure 12D:
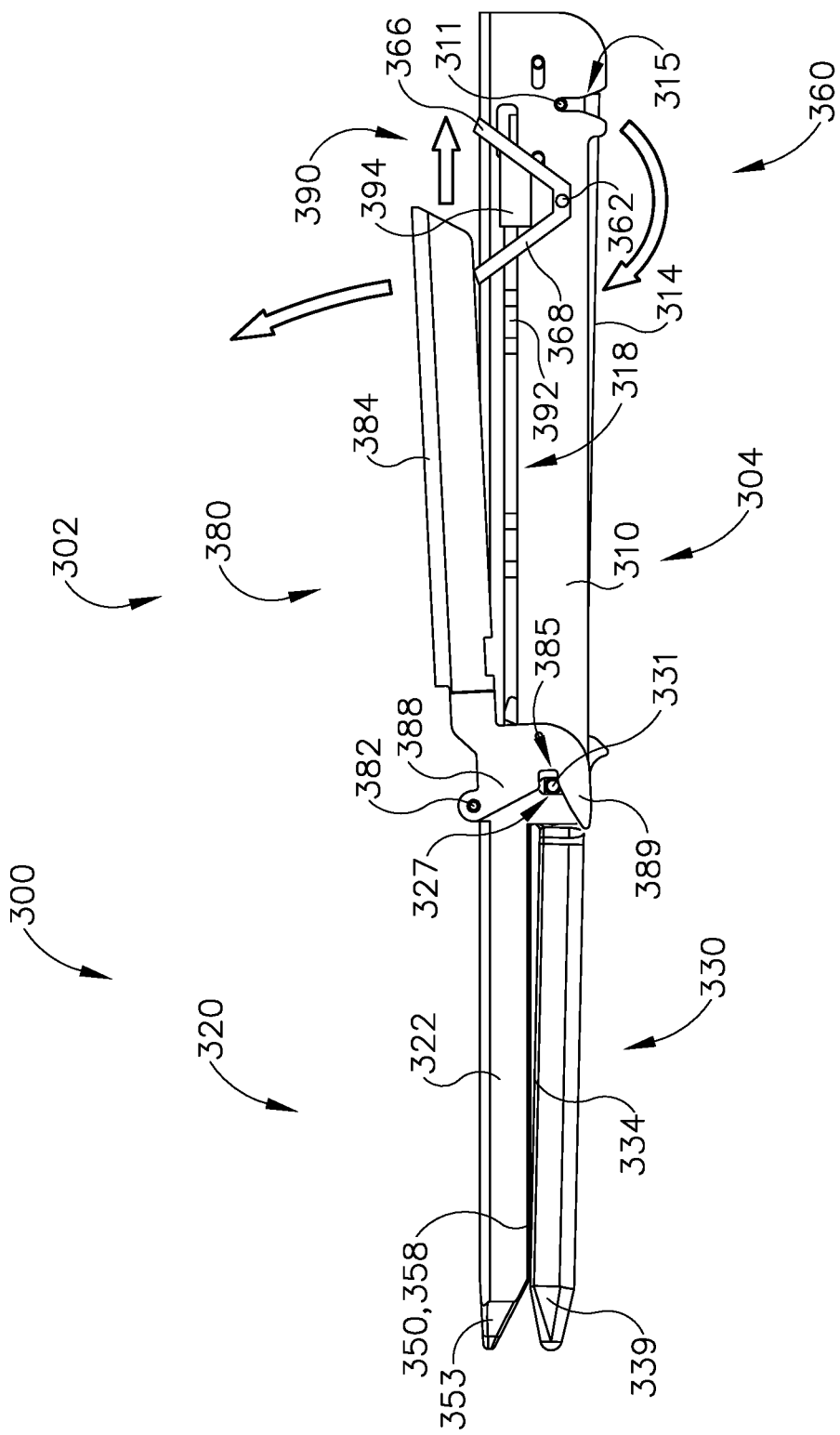
FIG. 12D depicts a side elevation view of the surgical instrument of FIG. 12A, where the firing assembly is in a post-fired position, where the release assembly is in a second position, and where the first portion is coupled with the second portion in a partially released position.

FIGS. 12A-12D show an exemplary use of instrument (300) to grasp tissue between staple deck (358) and anvil plate (334) in order to simultaneously sever and staple grasped tissue. FIG. 12A shows end effector (320) in the partially closed position and firing assembly (390) in a first position. End effector (320) may transition to the partially closed position in accordance with the teachings above. At this point, tissue may be located between the confines of staple deck (358) and anvil plate (334). As best shown between FIGS. 12A-12B, after hooks (389) initially contact latch projections (331), an operator may further rotate proximal extending arm (384) toward first proximal frame (310), causing distal latch body (388) to drive latch projections (331) along the surfaces of distal latch body (388) toward latch cutouts (385). As latch projections (331) are driven toward latch cutouts (385), anvil channel (330) and anvil plate (334) rotate further toward cartridge channel (322) and staple cartridge assembly (350) such that end effector (320) is in the fully closed position. Additionally, latch projections (331) are also driven toward recesses (327) of staple cartridge channel (322) such that each latch projection (331) is encompassed by a combination of the respective latch cutout (385) and recess (327), effectively latching end effector (320) into the fully closed position.

As shown in FIG. 12C, if an operator is satisfied with end effector (320) grasping tissue, the operator may translate actuator (394) of firing assembly (390) distally in order to simultaneously sever and staple tissue captured between staple deck (358) and anvil plate (334), in accordance with the description above. Alternatively, if the operator is not satisfied with end effector (320) grasping tissue, the operator may wish re-grasp tissue prior to actuating firing assembly (390) to simultaneously sever and staple tissue.

In either circumstance, it may be difficult for the operator to open end effector (320) by directly grasping proximal extending arm (384) to pivot latching lever (380). In order to overcome this initial difficulty, the operator may proximally translate actuator (394) to the position shown in FIG. 12D. Actuator (394) may abut against first leg (366) of rotating body (364), thereby pivoting rotating body (364) about pivot pin (362) in a first angular direction. This may cause second leg (368) to abut against proximal extending arm (384), which may help rotate latching lever (380) in a second angular direction about pivot pin (382) such that end effector (320) is urged toward the partially closed position. With release assembly (360) urging end effector (320) away from the fully closed position toward the partially closed position, the operator may more easily open end effector (320) by directly grasping and rotating proximal extending arm (384).

Second leg (368) may be dimensioned to abut against a portion of proximal extending arm (384) a sufficient distance away from pivot pin (382) to provide a mechanical advantage in urging latching lever (380) to open end effector (320). This mechanical advantage may help initially open, or unlock, end effector (320) from the fully closed position.

B. Exemplary Instrument with Alternative Release Assembly

FIGS. 13A-13D show an exemplary alternative instrument (400) that may be used in place of instrument (100) described above. Instrument (400) is substantially similar to instrument (100) described above, with differences elaborated below. Instrument (400) includes a first portion (402) having a staple cartridge channel (422), a second portion (404) having an anvil channel (430), a staple cartridge assembly (450) that may selectively couple with cartridge channel (422) of first portion (402), a firing assembly (490), and a release assembly (460).

First portion (402), second portion (404), staple cartridge assembly (450), and firing assembly (490) are substantially similar to first portion (102), second portion (104), staple cartridge assembly (150), and firing assembly (200) described above, respectively, with difference described below. Therefore, first portion (402) and staple cartridge assembly (450) may pivotably couple with second portion (404) to form an end effector (420) capable of clamping, severing, and stapling tissue captured between opposing halves of end effector (420). As will be described in greater detail below, release assembly (460) is configured to help urge latching lever (480) to initially pivot end effector (420) out of the fully closed position toward a partially closed position.

Firing assembly (490) includes an actuating beam (492), an actuator (494), and a staple sled assembly (not shown), substantially similar to actuating beam (202), actuator (204), and staple sled assembly (160) described above, respectively, with differences described below. In the current example, actuator (494) may not pivot to either lateral side of instrument (400). However, this is merely optional, as actuator (494) may be configured substantially similar to actuator (204) described above; or similar to any other actuator that would be apparent to one having ordinary skill in the art in view of the teachings herein.

First portion (402) includes a first proximal frame (410), staple cartridge channel (422), and a latching lever (480), which are substantially similar to first proximal frame (110), staple cartridge channel (122), and latching lever (180), described above, respectively, with differences elaborated below. In the present example, first proximal frame (410) and staple cartridge channel (422) are formed integrally so as to define an elongate cartridge channel member having a unitary construction. Latching lever (480) is pivotably coupled to either staple cartridge channel (422) or first proximal frame (410) via a pin (482).

First proximal frame (410) defines a channel that slidably houses actuating beam (492) of firing assembly (490). While first proximal frame (110) of instrument (100) includes one or more lateral pins, or projections (111) that are configured to be received in groove (115) of second portion (104); first proximal frame (410) of the current example defines grooves (415) that are configured to house lateral pins or projections (411) of second portion (404). Grooves (415) are configured to house pins (411) of second portion (404) in order to initially pivotably couple first and second portions (402, 404). Rather than both first portion (102) and second portion (104) defining lateral slot (118) while end effector (120) is in the fully closed position; first portion (402) of the current example defines lateral slot (418) alone, which defines a pathway for actuator (494) to travel.

Similar to staple cartridge channel (122) and staple cartridge assembly (150) described above, staple cartridge channel (422) is dimensioned to selectively couple and decouple with staple cartridge assembly (450). Cartridge assembly (450) includes a staple deck (458) and a distal nose (453) which are substantially similar to staple deck (158) and distal nose (153) described above. Staple cartridge channel (422) also defines notches or recesses (427) which are substantially similar to notches or recesses (127) described above. Therefore, recesses (427) are dimensioned to receive latch projections (431) of second portion (404) when second portion (404) pivots such that end effector (420) is in a fully closed position relative to first portion (402) (as shown in FIGS. 13B-13C).

Latching lever (480) includes a proximal extending arm (484) and a distal latch body (488), which are substantially similar to proximal extending arm (184) and distal latch body (188) described above, respectively. Therefore, distal latch body (488) includes a pair of hooks (489) that are substantially similar to hooks (189) described above. Additionally, distal latch body (488) also defines a corresponding pair of latch cutouts (485), which are substantially similar to latch cutouts (185) described above.

Second portion (404) of instrument (400) includes a second proximal frame (414), anvil channel (430), latch projections (431), and an anvil plate (434), which are substantially similar to second proximal frame (114), anvil channel (130), latch projections (131) and anvil plate (134) describe above, with differences described herein. Second portion (404) terminates distally in a distal nose (439), which extends distally from anvil channel (430) to provide an atraumatic tip.

As mentioned above, and as will be described in greater detail below, release assembly (460) is configured to help urge latching lever (480) to initially pivot end effector (420) out of a fully closed position toward a partially closed position. Release assembly (360) includes a cam surface (462) extending proximally from the open end of proximal extending arm (484). Cam surface (463) is dimensioned to abut against a corresponding cam surface (496) of actuator (494) as actuator (494) travels toward a proximal position along the path defined by lateral slot (418). In particular, proximal translation of actuator (494) will initially pivot latching lever (480) open such that end effector (420) transitions from the fully closed position toward the partially closed position. Afterwards, an operator may more easily open end effector (420) by directly grasping and rotating proximal extending arm (484).

Figure 13A:
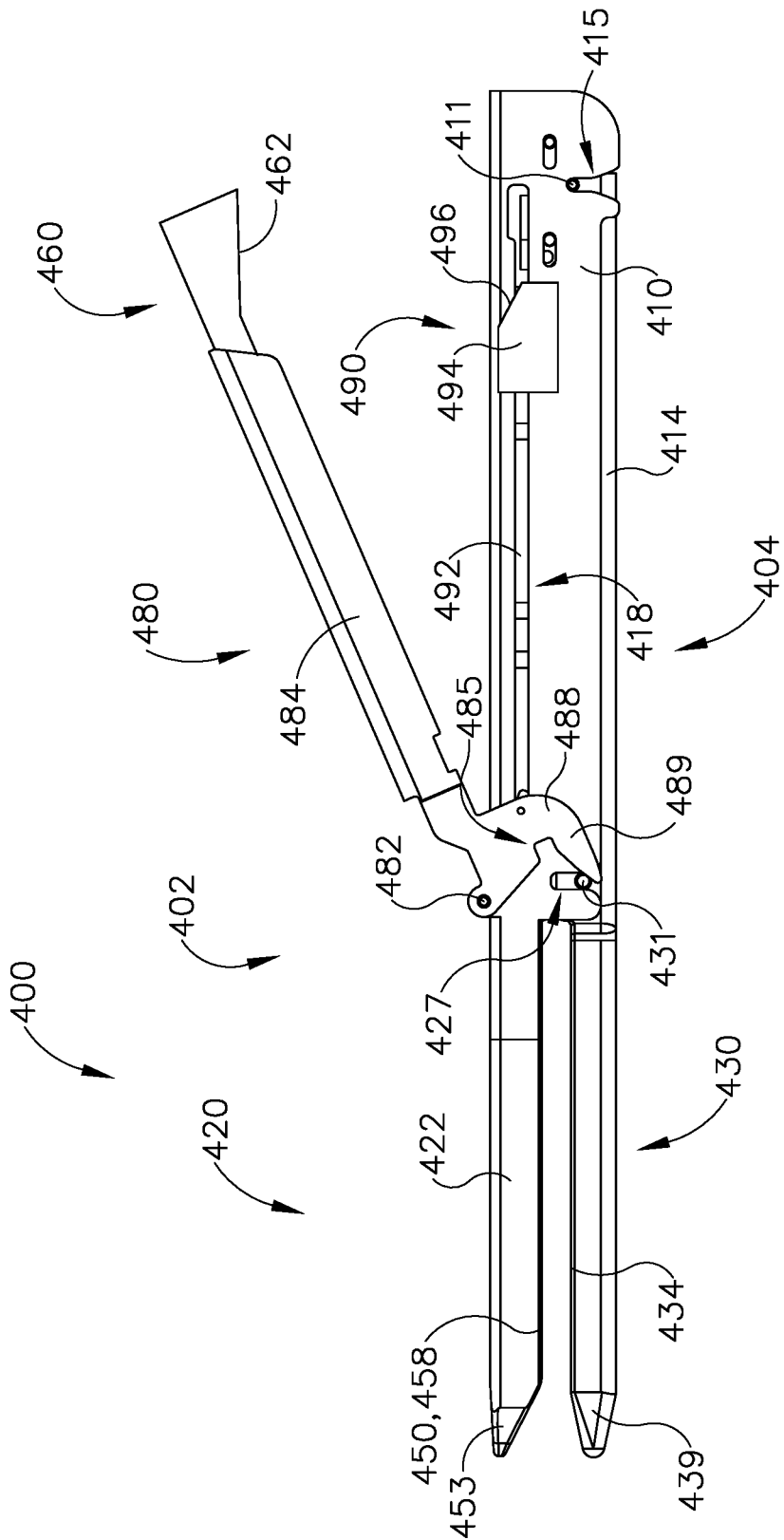
FIG. 13A depicts a side elevation view of an alternative surgical instrument having a first portion, a second portion, and a firing assembly, where the first portion is coupled with the second portion in a partially closed position, and where the firing assembly is in an unfired position.
Figure 13B:
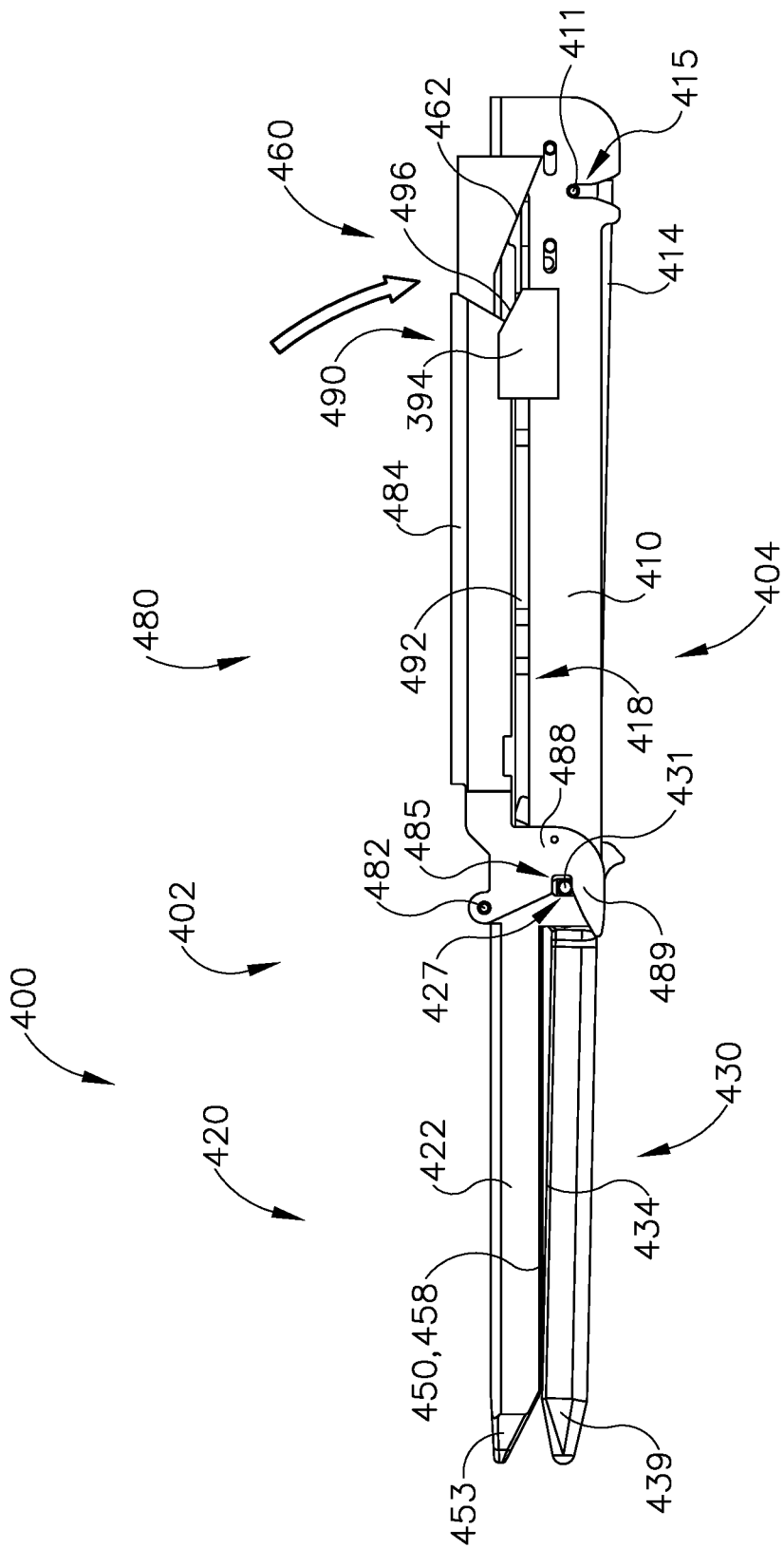
FIG. 13B depicts a side elevation view of the surgical instrument of FIG. 13A, where the first portion is coupled with the second portion in a fully closed position, where the firing assembly is in the unfired position.
Figure 13C:
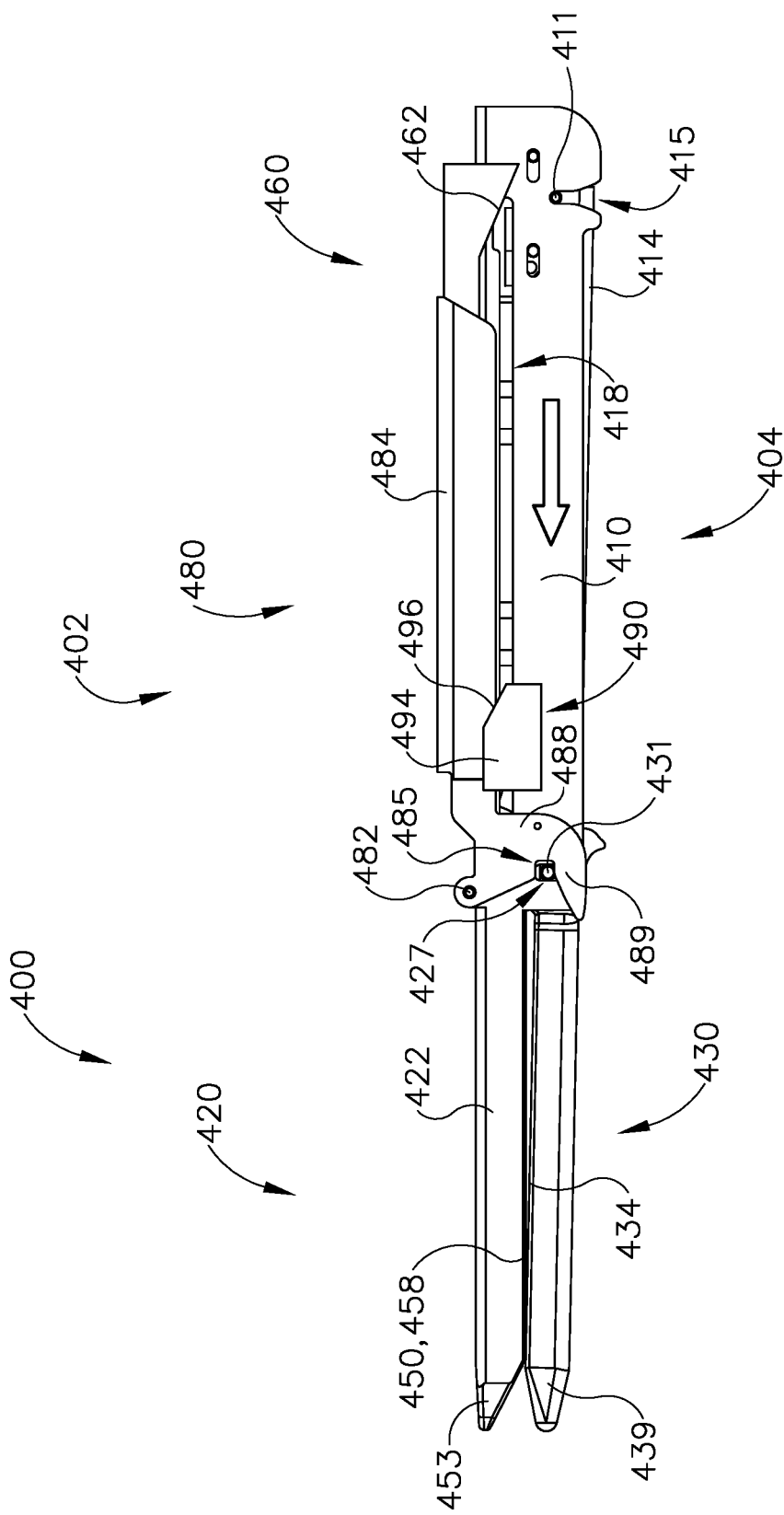
FIG. 13C depicts a side elevation view of the surgical instrument of FIG. 13A, where the first portion is coupled with the second portion in the fully closed position, where the firing assembly is in a fired position.
Figure 13D:
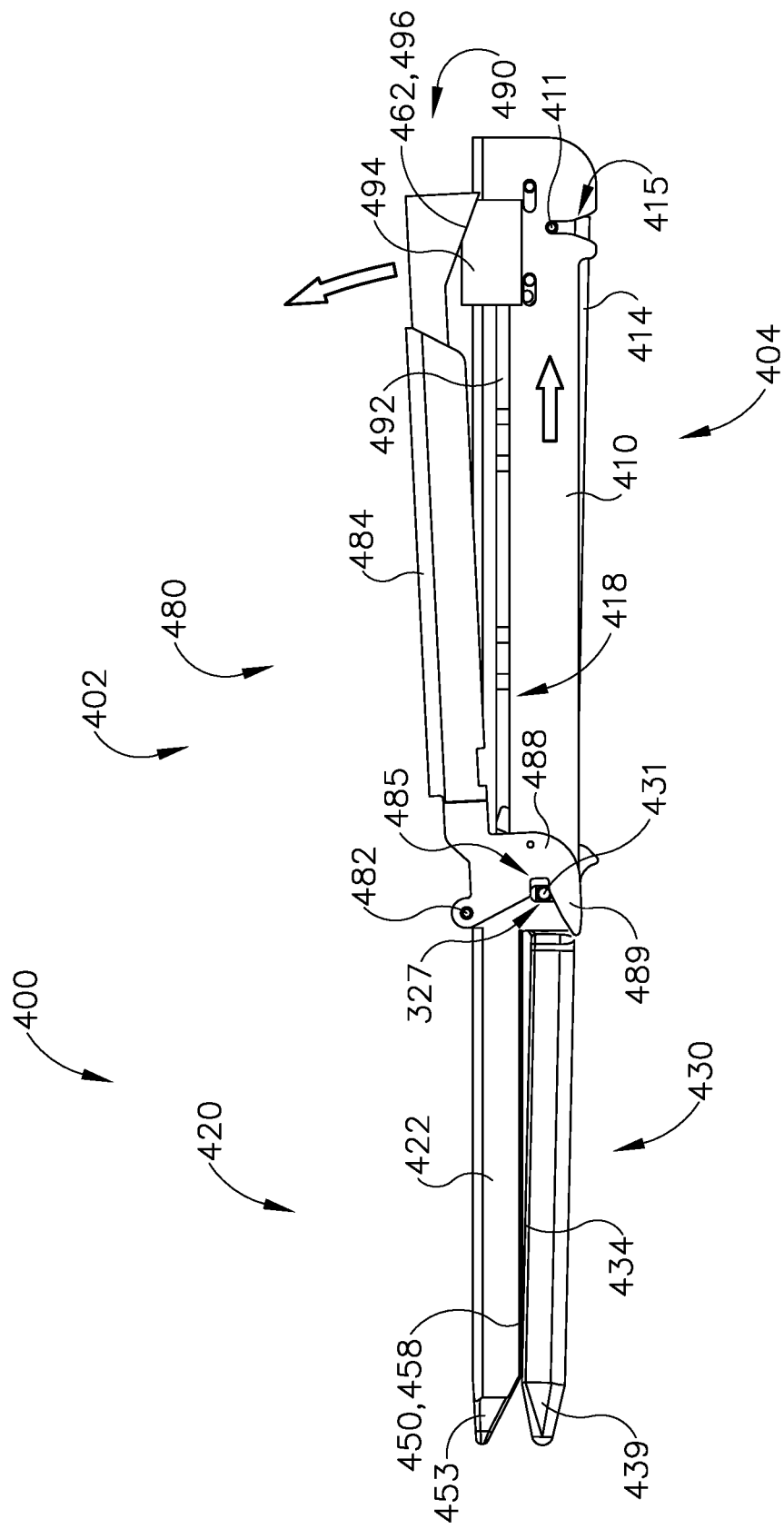
FIG. 13D depicts a side elevation view of the surgical instrument of FIG. 13A, where the firing assembly is in a post-fired position, where the first portion is coupled with the second portion in a partially released position.

FIGS. 13A-13D show an exemplary use of instrument (400) to grasp tissue between staple deck (458) and anvil plate (434) in order to simultaneously sever and staple grasped tissue. FIG. 13A shows end effector (420) in the partially closed position and firing assembly (490) in a first position. End effector (420) may transition to the partially closed position in accordance with the teachings above. At this point, tissue may be located between the confines of staple deck (458) and anvil plate (434). As best shown between FIGS. 13A-13B, after hooks (489) initially contact latch projections (431), an operator may further rotate proximal extending arm (484) toward first proximal frame (410), causing distal latch body (488) to drive latch projections (431) along the surfaces of distal latch body (488) toward latch cutouts (485). As latch projections (431) are driven toward latch cutouts (485), anvil channel (430) and anvil plate (434) rotate further toward cartridge channel (422) and staple cartridge assembly (450) such that end effector (420) is in the closed position. Additionally, latch projections (431) are also driven toward recesses (427) of staple cartridge channel (422) such that each latch projection (431) is encompassed by a combination of the respective latch cutout (485) and recess (427), effectively latching end effector (420) into the closed position.

As shown in FIG. 13C, if the operator is satisfied with end effector (420) grasping tissue, the operator may translate actuator (494) of firing assembly (490) distally in order to simultaneously sever and staple tissue captured between staple deck (458) and anvil plate (434), in accordance with the description above. Alternatively, if the operator is not satisfied with end effector (420) grasping tissue, the operator may wish re-grasp tissue prior to actuating firing assembly (490) to simultaneously sever and staple tissue.

In either circumstance, it may be difficult for the operator to open end effector (420) by directly grasping proximal extending arm (484) to pivot latching lever (480). In order to overcome this initial difficulty, the operator may proximally translate actuator (494) to the position shown in FIG. 13D. Cam surface (496) of actuator (494) may slide against cam surface (462) of release assembly (460), which may help rotate latching lever (480) in an angular direction about pivot pin (482) such that end effector (420) is urged toward the partially closed position. With camming surfaces (462, 496) urging end effector (420) away from the fully closed position toward the partially closed position, the operator may more easily open end effector (420) by directly grasping and rotating proximal extending arm (484).

Camming surface (462) of release assembly (460) may be located along proximally extending arm (484) a sufficient distance away from pivot pin (482) to provide a mechanical advantage in urging latching lever (480) to open end effector (420). This mechanical advantage may help initially open, or unlock, end effector (420) from the fully closed position.

C. Exemplary Instrument with Another Alternative Release Assembly

Figure 14:
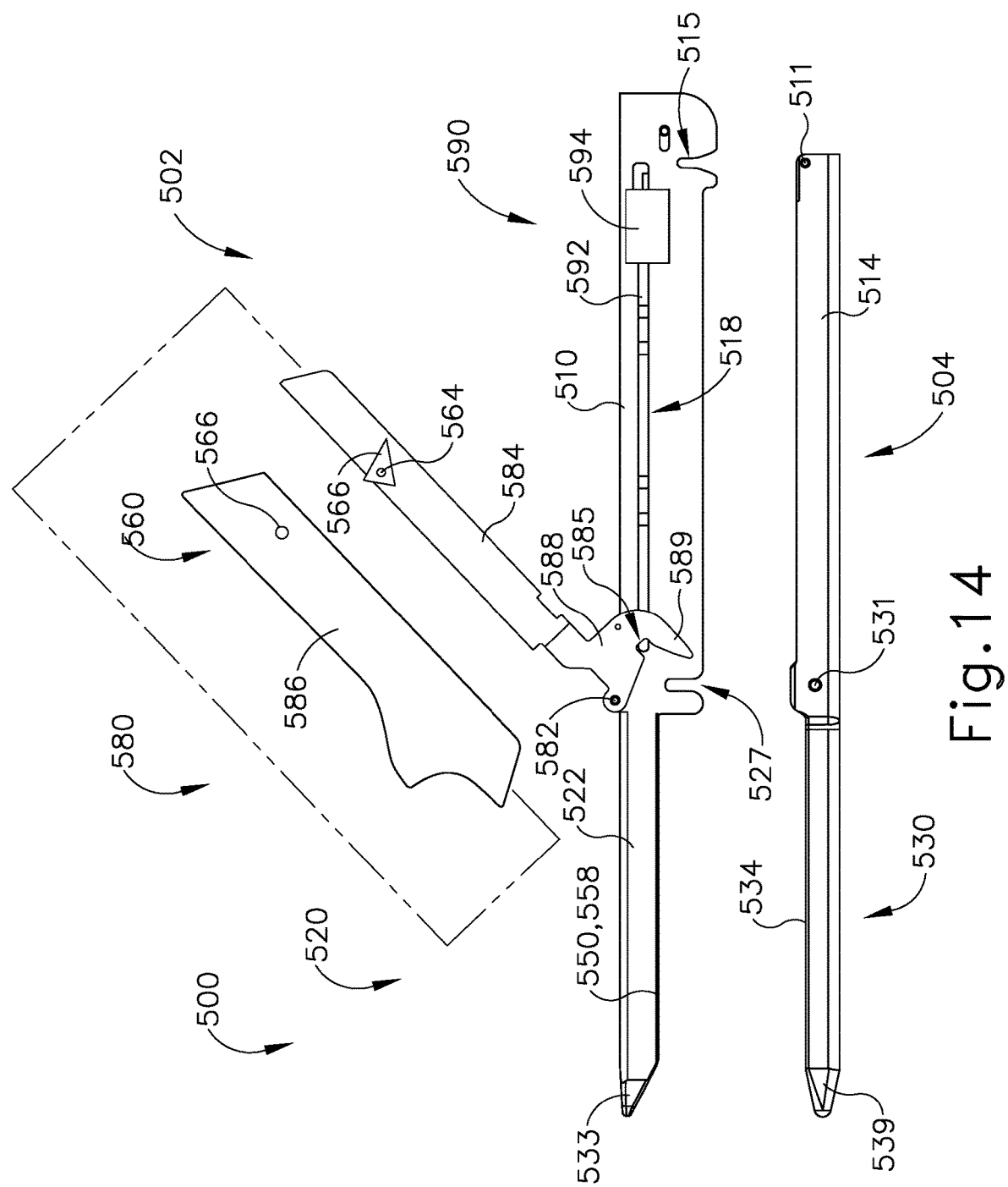
FIG. 14 depicts a partial exploded side elevation view of an alternative surgical instrument having a first portion, a second portion, a firing assembly, and a release assembly.

FIGS. 14-15C show an exemplary alternative instrument (500) that may be used in place of instrument (100) described above. Instrument (500) is substantially similar to instrument (100) described above, with differences elaborated below. Instrument (500) includes a first portion (502) having a staple cartridge channel (522), a second portion (504) having an anvil channel (530), a staple cartridge assembly (550) that may selectively couple with cartridge channel (522) of first portion (502), a firing assembly (590), and a release assembly (560).

First portion (502), second portion (504), staple cartridge assembly (550), and firing assembly (590) are substantially similar to first portion (102), second portion (104), staple cartridge assembly (150), and firing assembly (200) described above, respectively, with difference described below. Therefore, first portion (502) and staple cartridge assembly (550) may pivotably couple with second portion (504) to form an end effector (520) that is capable of clamping, severing, and stapling tissue captured between opposing halves of end effector (520). As will be described in greater detail below, release assembly (560) is configured to help urge latching lever (580) to initially pivot end effector (520) from a fully closed position to a partially closed position.

Firing assembly (590) includes an actuating beam (592), an actuator (594), and a staple sled assembly (not shown), substantially similar to actuating beam (202), actuator (204), and staple sled assembly (160) described above, respectively, with differences described below. In the current example, actuator (594) may not pivot to either lateral side of instrument (500). However, this is merely optional, as actuator (594) may be configured substantially similar to actuator (204) described above, or any other actuator that would be apparent to one having ordinary skill in the art in view of the teachings herein.

First portion (502) includes a first proximal frame (510), staple cartridge channel (522), a latching lever (580), and an arm cover (586), which are substantially similar to first proximal frame (110), staple cartridge channel (122), latching lever (180), and arm cover (186) described above, respectively, with differences elaborated below. In the present example, first proximal frame (510) and staple cartridge channel (522) are formed integrally so as to define an elongate cartridge channel member having a unitary construction. Latching lever (580) is pivotably coupled to either staple cartridge channel (522) or first proximal frame (510) via a pin (582). As will be described in greater detail below, arm cover (586) is slidably coupled to latching lever (580) such that arm cover (586) may at least partially actuate relative to latching lever (580).

First proximal frame (510) defines a channel that slidably houses actuating beam (592) of firing assembly (590). While first proximal frame (110) of instrument (100) includes one or more lateral pins, or projections (111) that were configured to be received in groove (115) of second portion (104); first proximal frame (510) of the current example defines grooves (515) that are configured to house lateral pins or projections (511) of second portion (504). Grooves (515) are configured to house pins (511) of second portion (504) in order to initially pivotably couple first and second portions (502, 504). Rather than both first portion (102) and second portion (104) defining lateral slot (118) while end effector (120) is in the fully closed position; first portion (502) of the current example defines lateral slot (518) alone, which defines a pathway for actuator (594) to travel.

Similar to staple cartridge channel (122) and staple cartridge assembly (150) described above, staple cartridge channel (522) is dimensioned to selectively couple and decouple with staple cartridge assembly (550). Cartridge assembly (550) includes a staple deck (558) and a distal nose (553) that are substantially similar to staple deck (158) and distal nose (153) described above. Staple cartridge channel (522) also defines notches or recesses (527) that are substantially similar to notches or recesses (127) described above. Therefore, recesses (527) are dimensioned to receive latch projections (531) of second portion (504) when second portion (504) pivots such that end effector (520) is in a fully closed position relative to first portion (502) (as shown in FIG. 15B).

Latching lever (580) includes a proximal extending arm (584) and a distal latch body (588), which are substantially similar to proximal extending arm (184) and distal latch body (188) described above, respectively, with differences elaborated below. Therefore, distal latch body (588) includes a pair of hooks (589) that are substantially similar to hooks (189) described above. Additionally, distal latch body (588)

also defines a corresponding pair of latch cutouts (585), which are substantially similar to latch cutouts (185) described above.

Second portion (504) of instrument (500) includes a second proximal frame (514), anvil channel (530), latch projections (531), and an anvil plate (534), which are substantially similar to second proximal frame (114), anvil channel (130), latch projections (131) and anvil plate (134) describe above, with differences described herein. Second portion (504) terminates distally in a distal nose (539), which extends distally from anvil channel (530) to provide an atraumatic tip.

As mentioned above, release assembly (560) is configured to help urge latching lever (580) to initially pivot end effector (520) out of a fully closed position toward a partially closed position. Release assembly (560) includes pivoting body (562) pivotably coupled to proximal extending arm (584) via a pivot pin (564), and a cam pin (566) associated with arm cover (586). Rotating body (564) is positioned on proximal extending arm (584) such that rotating body (564) is directly adjacent to first proximal frame (510) when end effector (520) is in the fully closed position. As mentioned above, arm cover (586) is slidably coupled to proximal extending arm (584) such that arm cover (586) may actuate relative to proximal extending arm (584). Cam pin (566) is positioned on proximal extending arm (584) such that actuation of arm cover (586) relative to arm (584) causes cam pin (566) is cam against pivoting body (562), thereby driving rotation of pivoting body (562) about rotation pin (564). In particular, translation of arm cover (586) relative to arm (586) will rotate pivoting body (562) about pivot pin (562) such that pivoting body (562) abuts against first proximal frame (510), thereby driving rotation of latching lever (580) open such that end effector (520) transitions from the fully closed position toward the partially closed position. Afterwards, an operator may more easily open end effector (520) by directly grasping and rotating proximal extending arm (584).

Figure 15A:
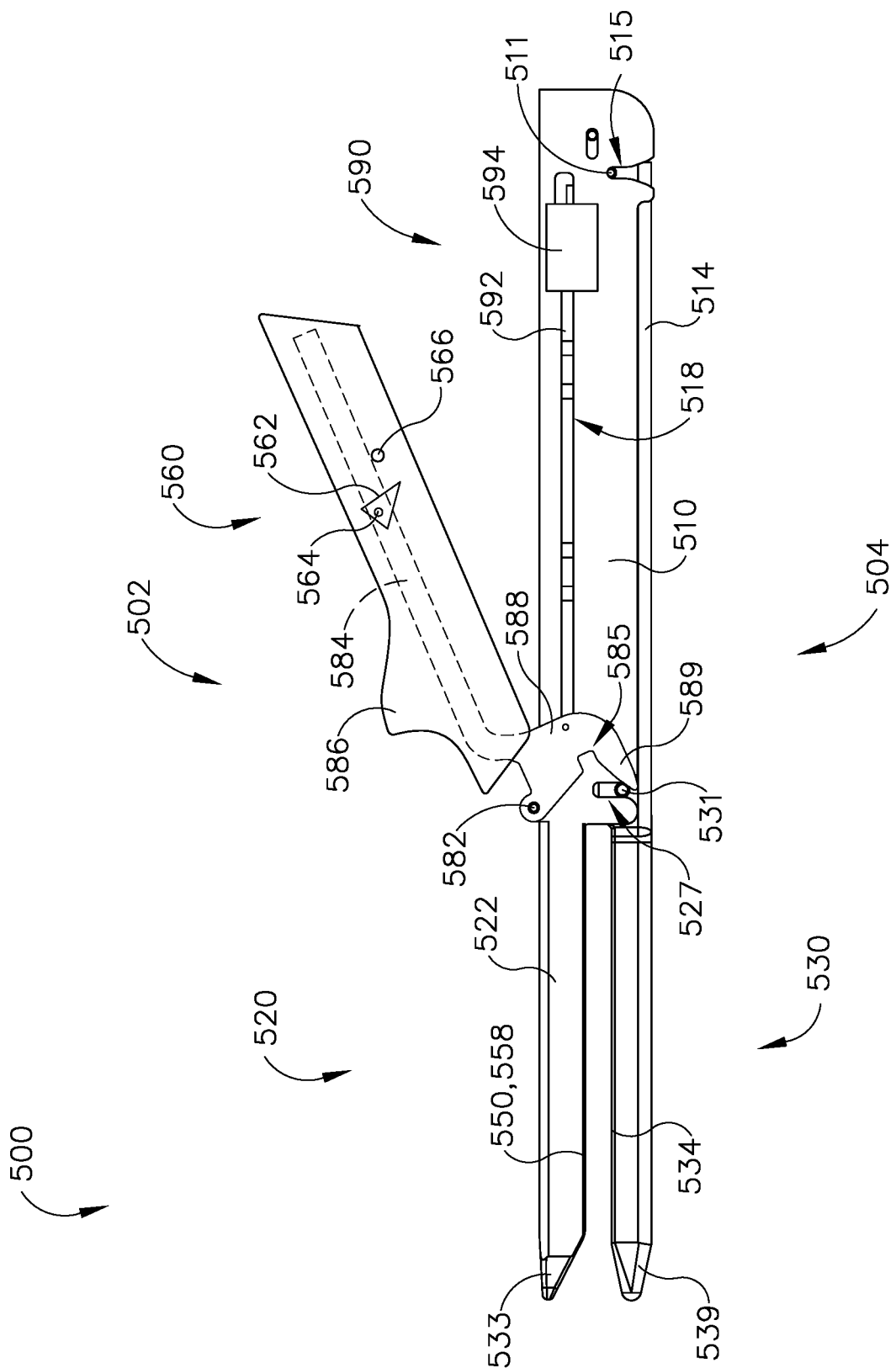
FIG. 15A depicts a side elevation view of the surgical instrument of FIG. 14, where the first portion is coupled with the second portion in a partially closed position, where the firing assembly is in an unfired position, and where the release assembly is in a first position.
Figure 15B:
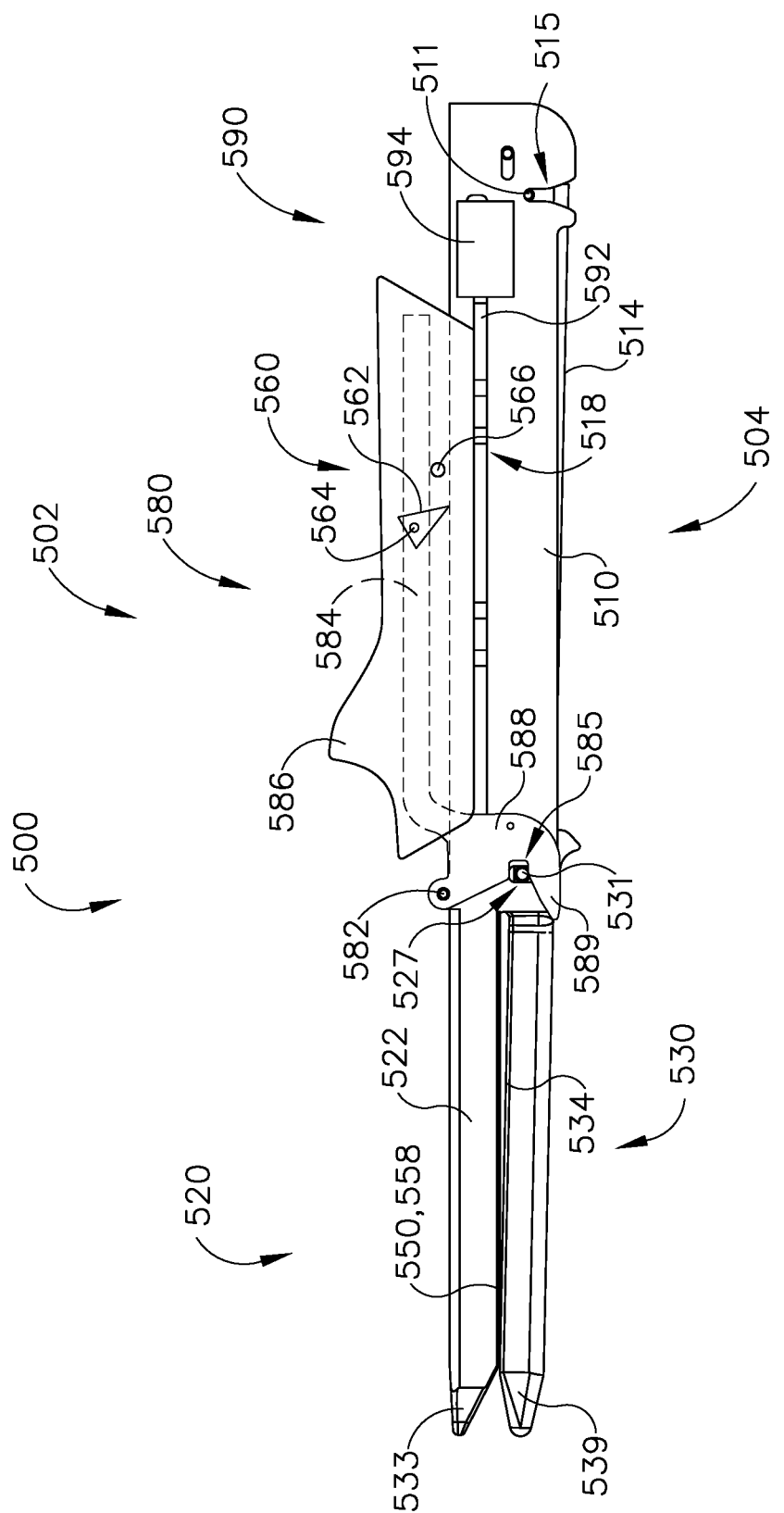
FIG. 15B depicts a side elevation view of the surgical instrument of FIG. 14, where the first portion is coupled with the second portion in a fully closed position, where the firing assembly is in the unfired position, and where the release assembly is in the first position.

FIGS. 15A-15C show an exemplary use of instrument (500) to grasp tissue between staple deck (558) and anvil plate (534) in order to simultaneously sever and staple grasped tissue. FIG. 15A shows end effector (520) in the partially closed position and firing assembly (590) in a first position. End effector (520) may transition to the partially closed position in accordance with the teachings above. At this point, tissue may be located between the confines of staple deck (558) and anvil plate (534). As best shown between FIGS. 15A-15B, after hooks (589) initially contact latch projections (531), an operator may further rotate proximal extending arm (584) toward first proximal frame (510), causing distal latch body (588) to drive latch projections (531) along the surfaces of distal latch body (588) toward latch cutouts (585). As latch projections (531) are driven toward latch cutouts (585), anvil channel (530) and anvil plate (534) rotate further toward cartridge channel (522) and staple cartridge assembly (550) such that end effector (520) is in the closed position. Additionally, latch projections (531) are also driven toward recesses (527) of staple cartridge channel (522) such that each latch projection (531) is encompassed by a combination of the respective latch cutout (585) and recess (527), effectively latching end effector (520) into the closed position.

If the operator is satisfied with end effector (52) grasping tissue, the operator may translate actuator (584) of firing assembly 9590) distally in order to simultaneously sever and staple tissue captured between staple deck (558) and anvil plate (534), in accordance with the description above. Alternatively, if the operator is not satisfied with end effector (520) grasping tissue, the operator may wish to re-grasp tissue prior to actuating firing assembly (590) to simultaneously sever and staple tissue.

In either circumstance, it may be difficult for the operator to open end effector (520) by directly grasping proximal extending arm (584) to pivot latching lever (580). In order to overcome this initial difficulty, as shown in FIG. 15C, the operator may actuate arm cover (586) relative to latching lever (580) to drive cam pin (566) against pivoting body (562). Pivoting body (562) may rotate into contact against first proximal frame (510), thereby driving proximal extending arm (584) and first proximal frame (510) away from each other, which urge end effector (520) toward the partially closed position. With pivoting body (562) rotating against first proximal frame (510) to urge end effector (520) away from the fully closed position, the operator may then more easily open end effector (520) by directly grasping and rotating proximal extending arm (585).

Rotating body (562) may be located along proximally extending arm (584) a sufficient distance away from pivot pin (582) to provide a mechanical advantage in urging latching lever (580) to open end effector (520). This mechanical advantage may help initially open, or unlock, end effector (520) from the fully closed position.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus, the apparatus comprising: (a) a handle assembly, wherein the handle assembly comprises: (i) a first arm, (ii) a second arm, wherein the second arm is configured to pivotably couple with the first arm at a proximal pivot location, and (iii) a latching lever pivotably coupled with the first arm at a distal pivot location; (b) an end effector, wherein the end effector comprises: (i) a first jaw extending distally from the first arm, and (ii) a second jaw extending distally from the second arm, wherein the second jaw is configured to pivot relative to the first jaw between an open configuration, a partially closed configuration, and a fully closed configuration, wherein the latching lever is configured engage the second arm or the second jaw to pivot the second jaw from the partially closed configuration toward the fully closed configuration; (c) a firing assembly configured to sever tissue captured between the first jaw and the second jaw in the fully closed configuration; and (d) a release assembly configured to urge the latching lever away from the first arm to pivot the second jaw from the fully closed position toward the partially closed position.

EXAMPLE 2

The apparatus of Example 1, wherein the first jaw is configured to receive a staple cartridge assembly housing a plurality of staples.

EXAMPLE 3

The apparatus of Example 2, wherein the staple cartridge assembly comprises a staple sled assembly.

EXAMPLE 4

The apparatus of any one or more of Examples 2 through 3, wherein the second jaw comprises an anvil, wherein the firing assembly is configured to fire the plurality of staples against the anvil when the second jaw is in the fully closed position.

EXAMPLE 5

The apparatus of any one or more of Examples 1 through 4, wherein the firing assembly comprises an actuator configured to translate relative to the first handle and the second handle.

EXAMPLE 6

The apparatus of Example 5, wherein the firing assembly further comprises a rotating body pivotally coupled to either the first handle or the second handle.

EXAMPLE 7

The apparatus of Example 6, wherein the rotating body comprises a first leg and a second leg, wherein the first leg is configured to abut against the actuator to pivot the rotating body, wherein the second leg is configured to urge the latching lever away from the first arm in response to the actuator pivoting the rotating body.

EXAMPLE 8

The apparatus of any one or more of Examples 5 through 7, wherein the release assembly comprises a camming surface extending from the latching lever, wherein the actuator is configured to abut against the camming to urge the latching lever away from the first arm.

EXAMPLE 9

The apparatus of any one or more of Examples 1 through 8, wherein the handle assembly further comprises an arm cover slidably attached to the latching lever.

EXAMPLE 10

The apparatus of Example 9, wherein the release assembly comprises a body pivotably attached to the latching lever.

EXAMPLE 11

The apparatus of Example 10, wherein the arm cover comprises a camming pin configured to pivot the body relative to the latching lever in response to movement of the arm cover relative to the latching lever.

EXAMPLE 12

The apparatus of Example 11, wherein the pivoting body is configured to urge the latching lever away from the first arm in response to the body pivoting.

EXAMPLE 13

The apparatus of any one or more of Examples 1 through 12, wherein the proximal pivot location comprises a transverse pin and a groove.

EXAMPLE 14

The apparatus of Example 12, wherein the transverse pin is associated with the first arm, wherein the second arm defines the groove.

EXAMPLE 15

The apparatus of any one or more of Examples 1 through 14, wherein the first arm defines a longitudinal channel that houses at least a portion of the firing assembly.

EXAMPLE 16

The apparatus of any one or more of Examples 1 through 15 wherein the second arm comprises a transverse pin, wherein the latching lever is configured to engage the transverse pin to pivot the second jaw from the partially closed configuration toward the fully closed configuration.

EXAMPLE 17

An apparatus, the apparatus comprising: (a) a first portion comprising: (i) a first handle, and (ii) a first jaw portion extending distally from the first handle; (b) a second portion comprising: (i) a second handle, (ii) a second jaw extending distally from the second handle, and (iii) a latching projection, wherein the second portion is configured to pivotably couple with the first portion at a proximal location; (c) a latching lever pivotably coupled with the first portion, wherein the latching lever is configured to engage the latching projection to pivot the first jaw and the second jaw from a partially closed configuration toward a fully closed configuration; (d) a firing assembly configured to sever tissue between the first jaw and the second jaw in the fully closed position; and (e) a release assembly configured to urge the latching lever away from the first portion to pivot the second jaw and the first jaw from the fully closed configuration toward the partially closed configuration.

EXAMPLE 18

The apparatus of Example 17, wherein the release assembly comprises a rotating body, wherein the firing assembly comprises an actuator, wherein the actuator is configured to pivot the rotating body the urge the latching lever away from the first portion.

EXAMPLE 19

The apparatus of any one or more of Examples 17 through 18, wherein the release assembly comprises a rotating body pivotably attached to the latching lever.

EXAMPLE 20

An apparatus, the apparatus comprising: (a) a first portion comprising: (i) a first handle, and (ii) a first jaw portion extending distally from the first handle; (b) a second portion comprising: (i) a second handle, (ii) a second jaw extending distally from the second handle, and (iii) a latching projection, wherein the second portion is configured to pivotably couple with the first portion at a proximal location in an open configuration; (c) a latching lever pivotably coupled with the first portion, wherein the latching lever is configured to pivot the first jaw and the second jaw from a partially closed configuration toward a fully closed configuration; and (d) a release assembly configured actuate relative to the latching lever in order to urge the latching lever away from the first portion to pivot the second jaw and the first jaw from the fully closed configuration toward the partially closed configuration.

IV. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application. Ser. No. 15/889,370, entitled "Lockout Assembly for Linear Surgical Stapler," filed Feb. 6, 2018, published as U.S. Pub. No. 2019/0239882 on Aug. 8, 2019, issued as U.S. Pat. No. 10,667,818 on Jun. 2, 2020; U.S. application. Ser. No. 15/889,374, entitled "Features to Align and Close Linear Surgical Stapler," filed Feb. 6, 2018, published as U.S. Pub. No. 2019/0239886 on Aug. 8, 2019, issued as U.S. Pat. No. 10,932,781 on Mar. 2, 2021; U.S. application. Ser. No. 15/889,376, entitled "Releasable Coupling Features for Proximal Portions of Linear Surgical Stapler," filed Feb. 6, 2018, published as U.S. Pub. No. 2019/0239883 on Aug. 8, 2019, issued as U.S. Pat. No. 10,898,197 on Jan. 26, 2021; U.S. application. Ser. No. 15/889,388, entitled "Firing Lever Assembly for Linear Surgical Stapler," filed Feb. 6, 2018, published as U.S. Pub. No. 2019/0239884 on Aug. 8, 2019, issued as U.S. Pat. No. 10,874,398 on Dec. 29, 2020; and U.S. application. Ser. No. 15/889,390, entitled "Clamping Mechanism for Linear Surgical Stapler," filed Feb. 6, 2018, published as U.S. Pub. No. 2019/0239885 on Aug. 8, 2019, issued as U.S. Pat. No. 10,687,819 on Jun. 23, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a handle assembly, comprising:
       (i) a first arm,
       (ii) a second arm, wherein the second arm is configured to pivotally couple with the first arm at a proximal pivot location, and (iii) a latching member movably coupled with the first arm between an unlatched position and a latched position;

(b) an end effector, comprising:
  (i) a first jaw extending distally from the first arm, and
  (ii) a second jaw extending distally from the second arm, wherein the latching member is configured to move from the unlatched position into the latched position to thereby pivot the second jaw relative to the first jaw from a partially closed configuration toward a fully closed configuration;

(c) a firing assembly configured to staple and sever tissue captured between the first jaw and the second jaw in the fully closed configuration; and (d) a release assembly, comprising:
  (i) a driving body configured to actuate relative to the handle assembly between a first position and a second position while the latching member is in the latched position, and
  (ii) a driven body, wherein the driving body is configured to engage the driven body while actuating between the first position and the second position in order to drive the latching member from the latching position toward the unlatched position.

2. The apparatus of claim 1, wherein the firing assembly comprises an actuator configured to translate relative to the handle assembly in order to sever tissue captured between the first jaw and the second jaw in the fully closed configuration.

3. The apparatus of claim 2, wherein the driving body is attached to the actuator such that translation of the actuator actuates the driving body between the first position and the second position.

4. The apparatus of claim 3, wherein the driven body is fixed to the latching member.

5. The apparatus of claim 4, wherein the driven body comprises a cam surface and the driving body comprises a corresponding cam surface configured to engage the cam surface of the driven body.

6. The apparatus of claim 5, wherein the cam surface is located at a proximal end of the latching member.

7. The apparatus of claim 6, wherein the corresponding cam surface is located on a proximal end of the actuator.

8. The apparatus of claim 3, wherein the driven body is pivotally coupled to the first arm.

9. The apparatus of claim 8, wherein the driven body comprises a first leg configured to engage the driving body, and a second leg configured to engage the latching member.

10. The apparatus of claim 1, wherein the driving body is slidably attached to the latching member.

11. The apparatus of claim 10, wherein the driven body is pivotally attached to the latching member.

12. The apparatus of claim 1, wherein the first jaw is configured to receive a staple cartridge assembly housing a plurality of staples.

13. The apparatus of claim 12, wherein the staple cartridge assembly comprises a staple sled assembly.

14. The apparatus of claim 12, wherein the second jaw comprises an anvil, wherein the firing assembly is configured to fire the plurality of staples against the anvil when the second jaw is in the fully closed position.

15. The apparatus of claim 1, wherein the first arm defines a groove, wherein the second arm comprises a projection dimensioned to fit within the groove at the proximal pivot location.

16. The apparatus of claim 1, wherein the second arm comprises a latch projection configured to engage the latching member.

17. An apparatus, the apparatus comprising:
(a) a first portion comprising:
  (i) a first handle, and
  (ii) a first jaw portion extending distally from the first handle;
(b) a second portion configured to pivotally couple with the first portion at a proximal pivot location, the second portion comprising:
  (i) a second handle,
  (ii) a second jaw portion extending distally from the second handle, and
  (iii) a latching projection;
(c) a latching member movably coupled with the first portion at a distal pivot location, wherein the latching member is configured to engage the latching projection and move from an unlatched position toward a latched position to thereby pivot the first jaw toward the second jaw from a partially closed position into a fully closed position;
(d) a firing assembly configured to staple and sever tissue between the first jaw and the second jaw in the fully closed position; and
(e) a release mechanism, comprising:
  a translating body configured to actuate between a first position and a second position, and
  (ii) a rotating body, wherein actuation of the translating body from the first position toward the second position is configured to drive rotation of the rotating body to thereby drive the latching member from the latching position toward the unlatched position.

18. The apparatus of claim 17, wherein the translating body is slidably coupled to the latching member.

19. The apparatus of claim 17, wherein the translating body is attached to the firing assembly.

20. An apparatus, the apparatus comprising:
(a) a first portion comprising:
  (i) a first handle, and
  (ii) a first jaw portion extending distally from the first handle;
(b) a second portion configured to pivotally couple with the first portion at a proximal pivot location, the second portion comprising:
  (i) a second handle,
  (ii) a second jaw portion extending distally from the second handle, and
  (iii) a latching projection;
(c) a latching member movably coupled with the first portion at a distal pivot location, wherein the latching member is configured to engage the latching projection and move from an unlatched position toward a latched position to thereby pivot the first jaw toward the second jaw from a partially closed position into a fully closed position;
(d) a firing assembly configured to staple and sever tissue between the first jaw and the second jaw in the fully closed position; and
(e) a release mechanism configured to actuate between a first position and a second position to generate a driving force to drive the latching lever from the latching position toward the unlatched position.

* * * * *